United States Patent [19]
Herlitschka et al.

[11] Patent Number: 6,114,146
[45] Date of Patent: *Sep. 5, 2000

[54] EXPRESSION PLASMID, A FUSION PROTEIN, A TRANSFECTED EUKARYOTIC CELL LINE, A METHOD OF PRODUCING FOREIGN PROTEINS, A FOREIGN PROTEIN PREPARATION AS WELL AS A PHARMACEUTICAL COMPOSITION

[75] Inventors: Sabine E. Herlitschka, Salzburg; Uwe Schlokat; Falko-Guenter Falkner, both of Orth/Donau; Friedrich Dorner, Vienna, all of Austria

[73] Assignee: Baxter Aktiengesellschaft, Vienna, Austria

[*] Notice: This patent issued on a continued prosecution application filed under 37 CFR 1.53(d), and is subject to the twenty year patent term provisions of 35 U.S.C. 154(a)(2).

[21] Appl. No.: 08/557,210

[22] Filed: Nov. 14, 1995

[30] Foreign Application Priority Data

Nov. 14, 1994 [AT] Austria .................................... 2099/94

[51] Int. Cl.$^7$ ................................................ C12P 21/02

[52] U.S. Cl. ..................... 435/69.7; 435/69.1; 435/69.8; 435/69.6

[58] Field of Search ................................. 435/69.7, 69.8, 435/358, 370, 69.1, 69.6; 530/350, 363, 381, 395; 514/2

[56] References Cited

U.S. PATENT DOCUMENTS

| | | | |
|---|---|---|---|
| 4,775,624 | 10/1988 | Bang et al. | 435/226 |
| 5,013,653 | 5/1991 | Huston et al. | 435/69.7 |
| 5,171,844 | 12/1992 | Van Ooyen et al. | 530/383 |
| 5,238,820 | 8/1993 | Kaufman | 435/69.1 |
| 5,519,115 | 5/1996 | Mapelli et al. | 530/324 |
| 5,591,827 | 1/1997 | Brakenhoff et al. | 530/351 |

FOREIGN PATENT DOCUMENTS

| | | |
|---|---|---|
| 0 247 145 | 2/1987 | European Pat. Off. . |
| 0 266 190 | 5/1988 | European Pat. Off. . |
| 0 294 910 | 12/1988 | European Pat. Off. . |
| 0 351 586 | 1/1990 | European Pat. Off. . |
| 42 28 458 | 6/1994 | Germany . |
| 86/06408 | 11/1986 | WIPO . |
| 90/01550 | 2/1990 | WIPO . |
| 91/11519 | 8/1991 | WIPO . |
| 92/08796 | 5/1992 | WIPO . |
| 93/03143 | 2/1993 | WIPO . |
| 94/05785 | 3/1994 | WIPO . |
| 94/24870 | 11/1994 | WIPO . |

OTHER PUBLICATIONS

Germann et al., "Retroviral Transfer of a Chimeric Multidrug Resistance–Adenosine Deaminase Gene", FASEB Journal, No. 4, pp. 1501–1507 (1990).

Sugimoto et al., "Efficient Expression of Drug–Selectable Genes in Retroviral Vectors Under Control of an Internal Ribosome Entry Site", Biotechnology, vol. 12, No. 7, pp. 694–698, (1994).

Kaufman et al., "Expression, Purification, and Characterization of Recombinant Carboxylated Factor IX Synthesized in Chinese Hamster Ovary Cells", J. Bio. Chem., vol. 261, No. 21, pp. 9622–9628, (1986).

Southern et al., "Transformation of Mammalian Cells to Antibiotic Resistance with a Bacterial Gene Under Control of the SV40 Early Region Promoter", J. Molecular & Applied Genetics, vol. 1, pp. 327–341, (1982).

Blochlinger et al., "Hygromycin B Phosphotransferase as a Selectable Marker for DNA Transfer Experiments with Higher Eucaryotic Cells", Molecular and Cellular Biology, pp. 2929–2931, (1984).

McIvor et al., "Isolation & Characterization of a Variant Dihydrofolate Reductase cDNA from Methotrexate–Resistant Murine L5178Y Cells", Nucleic Acids Res., vol. 18, No. 23, pp. 7025–7032, (1990).

Kim et al., Stable Reduction of Thymidine Kinase Activity in Cells Expressing High Levels of Anti–Sense RNA, Cell, vol. 42, pp. 129–138, (1985).

Wirth et al., "Genetic Engineering of Animal Cells", Genetic Engineering of Animals, pp. 1–82, (1993).

Kaufman, "Selection and Coamplification of Heterologous Genes in Mammalian Cells", Gene Selection and Coamplification, Methods in Enzymology, vol. 185, pp. 537–566, (1990).

McCormick et al., "Inducible Expression of Amplified Human Beta Interferon Genes in CHO Cells", Molecular and Cellular Biology, pp. 166–172, (1984).

Haynes, et al., "Constitutive, Long–term Production of Human Interferons by Hamster Cells Containing Multiple copies of a Cloned Interferon Gene", Nucleic Acids Res., vol. 11, No. 3 (1983).

Onomichi et al., "Expression of Amplified cDNA & Genomic Sequence Encoding Human Interleukin 2 in Chinese Hamster Ovary Cells", J. Biochem., vol. 102, pp. 123–131, (1987).

Walls et al., "Amplification of Multicistronic Plasmids in the Human 293 Cell Line & Secretion of Correctly Processed Recombinant Human Protein C", Gene, vol. 81, pp. 139–149, (1989).

Wernicke et al., "Generation of Recombination CHO(dhfr–) Cell Lines by Single Selection for dhfr+ Transformants", Analytical Biochem., vol. 203, pp. 146–150, (1992).

(List continued on next page.)

Primary Examiner—Karen Cochrane Carlson
Assistant Examiner—Gabriele E. Bugaisky
Attorney, Agent, or Firm—Foley & Lardner

[57] ABSTRACT

The invention describes an expression plasmid containing a dicistronic transcription/translation unit, which unit comprises a sequence for a foreign protein and a sequence for a fusion protein, the fusion protein containing at least one selection marker and at least one amplification marker. Further described is a method of producing foreign proteins by using the plasmids according to the invention, as well as cell lines transformed with the plasmid according to the invention.

31 Claims, 19 Drawing Sheets

OTHER PUBLICATIONS

Kaufman et al., "Translational Efficiency of Polycistronic mRNAs and Their Utilization to Express Hetero. Genes in Mammalian Cells", EMBO Journal, vol. 6, No. 1, pp. 187–193, (1987).

Kozak et al., "Effects of Intercistronic Length on the Efficiency of Reinitiation by Eurcaryotic Ribosomes", Molecular and Cellular Biology, pp. 3438–3445, (1987).

Pelletier et al., "Internal Initiation of Translation of Eukaryotic MRNA Directed by a Sequence Derived From Poliovirus RNA", Nature, vol. 334, pp. 320–325, (1988).

Jang et al., "Initiation of Protein Synthesis by Internal Entry of Ribosomes into the 5' Nontranslated Region of Encephalomyocarditis Virus RNA In Vivo", J. of Virology, pp. 1651–1660, (1989).

Kaufman et al., "Improved Vectors for Stable Expression of Foreign Genese in Mammalian Cells by Use of the Untranslated Leader Sequence From EMC Virus", Nucleic Acids Res., vol. 19, No. 16, pp. 4485–4490, (1991).

Schwartz et al., "A Dominant Positive and Negative Selectable Gene for Use in Mammalian Cells", Proc. Natl. Acad. Sci., vol. 88, pp. 10416–10420, (1991).

Jorgensen et al., "Expression of completely γ–Carboxylated Recombinant Human Prothrombin", J. of Bio. Chem., vol. 262, No. 14, pp. 6729–6734, (1987).

Falkner et al., "High Level Expression of Active Human Prothrombin in a Vaccina Virus Expression System", Thrombosis and Haemostasis, vol. 68, No. 2, pp. 119–124, (1992).

Kaufman et al., "Synthesis, Processing, and Secretion of Recombinant Human Factor VIII Expressed in Mammalian Cells", J. of Bio. Chem., vol. 263, No. 13, pp. 6352–6362, (1988).

Eaton et al., "Construction and Characterization of an Active Factor VIII Variant Lacking the Central One–Third of the Molecule", Biochemistry, vol. 25, No. 26, pp. 8343–8347, (1986).

Mertens et al., "Biol. Acitiv. of Recombinant Factor VIII Vari. Lacking the Centr. B–Domain 7 Heavy–Chain Sequ. Lys713–Arg740: Discordant In Vitro & In Vivo Activity", Brit. J. Hematol., vol. 85, pp. 133–142, (1993).

Toole et al., "A Large Region (=95 kDa) of Human Factor VIII Dispensable for In Vitro Procoagulant Activity", Proc. Natl. Acad. Sci. USA, vol. 83, pp. 5939–5942, (1986).

Pittman et al., "Biochemical, Immunological, & In Vivo Funct. Characterization B–Domain–Deleted Factor VIII" Blood, vol. 81, No. 11, pp. 2925–2935, (1993).

Balland et al., "Characterization of Two Differently Processed Forms of Human Recombinant Factor IX Synthes. in CHO Cells Trans. With A Polycistronic Vector", Eur. J. Biochem., vol. 172, pp. 565–572, (1988).

Grinnell et al, "Native and Modified Recombinant Human Protein C: Function, Secretion, and Posttranslational Modifications", Adv. Appl. Biotech. Ser., pp. 29–63, (1990).

Urlaub et al., "Isolation of Chinese Hamster Cell Mutants Deficient In Dihydrofolate Reductase Activity", Proc. Natl. Acad. Sci. USA, vol. 77, No. 7, pp. 4216–4220, (1980).

MacGregor et al., "Construction of Plasmids That Express E. Coli B–Galactosidase In Mammalian Cells", Nucleic Acids Research, vol. 17, No. 6, p. 1, (1989).

Kaufman et al., "Construction of a Modular Dihydrofolate Reductase cDNA Gene: Analysis of Signals Utilized for Efficient Expression", Molecular & Cell. Biol., pp. 1304–1319, (1982).

Towbin et al., "Electrophoretic Transfer of Proteins From Polyacrylamide Gels to Nitrocellulose Sheets: Procedure and Some Applications", Proc. Natl. Acad. Sci. USA, vol. 76, No. 9, pp. 4350–4354, (1979).

Leyte et al., "Inhibition of Human Coagulation Factor VIII by Monoclonal Antibodies", Biochem. J., vol. 263, pp. 187–194, (1989).

Neumann et al., "Gene Transfer Into Mouse Lyoma Cells by Electroporation In High Electric Fields", EMBO Journal, vol. 1, No. 7, pp. 841–845, (1982).

Stel et al., "Charac. 25 Monoclonal Antibodies Fact. VII-I–von Willebrand Fact.: Relat. Betw. Ristocetin–Induced Platelet Aggrega & Platelet Adherence Subendoth.", Blood, vol. 63, No. 6, pp. 1408–1416, (1984).

Schmike et al., "Chromosomal and Extrachromosomal Localization of Amplified Dihydrofolate Reductase Genes in Cultured Mammalian Cells", CSHSA, vol. 45, pp. 785–797, (1988).

Kaufman et al., "Evolution of Chromosomal Regions Containing Transfected and Amplified Dihydrofolate Reductase Sequences", Molecular and Cellular Biology, pp. 699–711, (1983).

Leyte et al., "Sulfation of $Tyr^{1680}$ of Human Blood Coagulation Factor VIII Is Esential for the Interaction of Factor VIII with von Willebrand Factor", Journal of Bio. Chem., vol. 266, No. 2, pp. 740–746, (1991).

Gunning et al., "A Human B–Actin Expression Vector System Directs High–Level Accumulation of Antisense Transcripts", Proc. Natl. Acad. Sci. USA, vol. 84, pp. 4831–4835, (1987).

Fischer et al., "Structural Analysis of Recombinant von Willebrand Factor: Identification of Hetero– and Homo–Dimers", FEBS Letters 351, pp. 345–348, (1994).

Laemmli et al., "Cleavage of Structural Proteins During the Assembly of the Head of Bacteriophage T4", Nature, vol. 227, pp. 680–685, (1970).

Ehrlich et al., "Direct Expression of Recombinant Activated Human Protein C, a Serine Protease" The Journal of Biological Chemistry, vol. 264, No. 24, pp. 14298–14304, (1989).

Beckmann et al., "Struct & Evolu. of 461 Amino Acid Human Protein C Precursor & Messenger RNA, Based Upon DNA Sequence of Cloned Human Liver cDNAs", Nucl. Acids Res., vol. 13, No. 14, pp. 5233–5247, (1985).

Foster et al., "Characterization of A cDNA Coding for Human Protein C", Proc. Natl. Acad. Sci. USA, vol. 81, pp. 4766–4770, (1984).

Moss et al., "New Mammalian Expression Vectors", Nature, vol. 348, pp. 91–92, (1990).

Lawn et al., "The Sequence of Human Serum Albumin cDNA and its Expression E. coli", Nucleic Acids Research vol. 9, No. 22, pp. 6103–6114, (1981).

Dugaiczyk et al., "Nucleotide Sequence and the Encoded Amino Acids of Human Serum Albumin mRNA", Proc. Natl. Acad. Sci. USA, pp. 71–75, (1982).

Shen et al. Construction and Expression of an adenosine deaminase::lacZ fusion gene. Gene. vol. 98, pp. 283–287, 1991.

Yeung et al. Identification of functional murine adenosine deaminase cDNA clones by complementation in *Escherichia coli*. The Journal of Biological Chemistry. vol. 260, No. 18, pp. 10299–10307, Aug. 25, 1985.

Kaufman et al. Selection and amplification of heterologous genes encoding adenosine deaminase in mammalian cells. Proceedings of the National Academy of Sciences, USA. vol. 83, No. 10, pp. 3136–3140, May 1986.

FIG. 5A

```
MVRPLNCIVA VSQNMGIGKN GDLPWPPLRN EFKYFQRMTT TSSVEGKQNL

VIMGRKTWFS IPEKNRPLKD RINIVLSREL KEPPRGAHFL AKSLDDALRL

IEQPELASKV DMVWIVGGSS VYQEAMNQPG HLRLFVTRIM QEFESDTFFP

EIDLGKYKLL PEYPGVLSEV QEEKGIKYKF EVYEKKPELT ATSVEKFLIE

KFDSVSDLMQ LSEGEESRAF SFDVGGRGYV LRVNSCADGF YKDRYVYRHF

ASAALPIPEV LDIGEFSESL TYCISRRAQG VTLQDLPETE LPAVLQPVAE

AMDAIAAADL SQTSGFGPFG PQGIGQYTTW RDFICAIADP HVYHWQTVMD

DTVSASVAQA LDELMLWAED CPEVRHLVHA DFGSNNVLTD NGRITAVIDW

SEAMFGDSQY EVANIFFWRP WLACMEQQTR YFERRHPELA GSPRLRAYML

RIGLDQLYQS LVDGNFDDAA WAQGRCDAIV RSGAGTVGRT QIARRSAAVW

TDGCVEVLAD SGNRRPSTRP RAKE
```

FIG. 5B

MVRPLNCIVA VSQNMGIGKN GDLPWPPLRN EFKYFQRMTT TSSVEGKQNL

VIMGRKTWFS IPEKNRPLKD RINIVLSREL KEPPRGAHFL AKSLDDALRL

IEQPELASKV DMVWIVGGSS VYQEAMNQPG HLRLFVTRIM QEFESDTFFP

EIDLGKYKLL PEYPGVLSEV QEEKGIKYKF EVYEKKGRLR TGGGGGNRRI
                                            Glycine Spacer

PPELTATSVE KFLIEKFDSV SDLMQLSEGE ESRAFSFDVG GRGYVLRVNS

CADGFYKDRY VYRHFASAAL PIPEVLDIGE FSESLTYCIS RRAQGVTLQD

LPETELPAVL QPVAEAMDAI AAADLSQTSG FGPFGPQGIG QYTTWRDFIC

AIADPHVYHW QTVMDDTVSA SVAQALDELM LWAEDCPEVR HLVHADFGSN

NVLTDNGRIT AVIDWSEAMF GDSQYEVANI FFWRPWLACM EQQTRYFERR

HPELAGSPRL RAYMLRIGLD QLYQSLVDGN FDDAAWAQGR CDAIVRSGAG

TVGRTQIARR SAAVWTDGCV EVLADSGNRR PSTRPRAKE

FIG. 5C

```
MVRPLNCIVA VSQNMGIGKN GDLPWPPLRN EFKYFQRMTT TSSVEGKQNL

VIMGRKTWFS IPEKNRPLKD RINIVLSREL KEPPRGAHFL AKSLDDALRL

IEQPELASKV DMVWIVGGSS VYQEAMNQPG HLRLFVTRIM QEFESDTFFP

EIDLGKYKLL PEYPGVLSEV QEEKGIKYKF EVYEKKGRFP PPPPVRNRRI
                                            ProlineSpacer

PPELTATSVE KFLIEKFDSV SDLMQLSEGE ESRAFSFDVG GRGYVLRVNS

CADGFYKDRY VYRHFASAAL PIPEVLDIGE FSESLTYCIS RRAQGVTLQD

LPETELPAVL QPVAEAMDAI AAADLSQTSG FGPFGPQGIG QYTTWRDFIC

AIADPHVYHW QTVMDDTVSA SVAQALDELM LWAEDCPEVR HLVHADFGSN

NVLTDNGRIT AVIDWSEAMF GDSQYEVANI FFWRPWLACM EQQTRYFERR

HPELAGSPRL RAYMLRIGLD QLYQSLVDGN FDDAAWAQGR CDAIVRSGAG

TVGRTQIARR SAAVWTDGCV EVLADSGNRR PSTRPRAKE
```

EXPRESSION PLASMID, A FUSION PROTEIN, A TRANSFECTED EUKARYOTIC CELL LINE, A METHOD OF PRODUCING FOREIGN PROTEINS, A FOREIGN PROTEIN PREPARATION AS WELL AS A PHARMACEUTICAL COMPOSITION

The invention relates to expression plasmids containing a dicistronic transcription/translation unit.

In the field of biotechnology, the expression of proteins in eukaryotic cell systems has become a common method. The plasmid vectors most frequently used have been constructed for the efficient expression of foreign proteins and contain i. a. the following genetic elements: a bacterial origin of replication, (ori), a eukaryotic promoter for transcription initiation of the foreign gene, eukaryotic mRNA-processing signals, polylinkers containing multiple restriction endonuclease cleavage sites for insertion of the foreign DNA, and selection and amplification markers for the selection and identification of cells which have taken up transfected DNA.

The selection marker confers upon the target cell the capability to survive in a given medium. This can be effected by supplementing a missing metabolic function or by the property of growing despite the presence of a toxic agent.

Recessive resistance genes can only be used in such host systems which are deficient in respect of the examined selection activity. The dihydrofolate reductase gene (dhfr) is the recessive selection marker most frequently used. Its efficient use is restricted to dhfr-deficient CHO cells. The dihydrofolate reductase catalyzes the reduction of folate to tetrahydrofolate ($FH_4$). $FH_4$ in turn is required for the biosynthesis of glycine from serine, thymidine monophosphate from deoxyuridine-monophosphate and for the biosynthesis of purine. Methotrexate (MTX), a folate analogue, binds to and inhibits the dihydrofolate reductase and thus causes the cell death of the exposed cells.

Dominant resistance genes are being used irrespective of the genotype of the host system and thus can be used universally in all cells. In this group are i.a. the adenosine-deaminase gene (Kaufman et al, J. Biol. Chem. 261:9622, 1986), the antibiotics resistance genes, such as, e.g., the neomycin phosphotransferase gene (Southern and Berg, J. Mol. Appl. Genet. 1:327, 1982), and the hygromycin B phosphotransferase gene (hph; Blochinger and Diggelmann, Mol. Cell. Biol. 4:2929, 1984).

Although the dhfr gene is mainly used as a recessive selection marker in dhfr-deficient cells, there are ways of utilizing the dhfr gene under certain pre-requisites also in cells having endogenous dhfr activity. Thus, e.g., transfected cells can grow in moderate methotrexate concentrations by using a strong promoter for the transcription of the endogenous dhfr gene. In this case, the MTX concentration must be higher than the MTX concentration that can be compensated by the endogenous dhfr gene. With this method, however, one has to put up with many false positive cell clones.

Furthermore, it is possible to use a mutant dhfr gene as the dominant selection marker (Simonsen and Levinson, PNAS 80: 2495; 1983, McIvor and Simonsen, NAR 18, 7025 ff, 1990). These mutant dhfr genes have a clearly lower affinity to MTX, and thus it is possible to use higher MTX concentrations than necessary to inactivate the endogenous dihydrofolate reductase.

Another way is the cotransfection of the DHFR gene with an additional dominant selection marker, e.g. the neomycin phosphotransferase gene for the resistance to geneticin (Southern, supra), the subsequent transfer of the geneticin-resistant transfected cells into methotrexate-containing medium (Kim and Wold, Cell 42: 129, 1985). After a cotransfection, however, often false positive clones are identified which have only taken up the dominant selection marker plasmid.

By an increased selection pressure, an amplification of the resistance gene and of the adjacent genes can be observed. With increasing MTX concentrations, the dhfr wild type gene can be amplified 1000 fold and more, over many rounds of increasing amplification pressure, while amplifiable dominant markers, such as the mutant dhfr gene or the adenosine deaminase gene, can be amplified only to a limited extent, such as two or three steps. By increasing the concentration of hygromycin B, amplification could not be observed so far (Wirth and Hauser, "Genetic Engineering of Animal Cells" in "Genetic Engineering of Animals" Edt. P ühler, Publishers Chemie Weinheim, (1993), 1–82; Kaufman, Methods in Enzymology, Vol. 185, (1990), 537–566).

The dhfr selection/MTX amplification-system thus represents the route most frequently used for establishing highly expressing cell lines by using the coexpression of heterologous genes.

Because of its recessive manner of action, however, its use is primarily restricted to dhfr-deficient CHO cells.

First attempts for the coexpression and co-amplification of dhfr and a foreign gene have been made by cotransfecting two plasmids. In this instance, the plasmids are transfected into dhfr-deficient cells. Co-transfection, however, involves the disadvantage that, on account of selection, a part of the transfected cells only take up the dhfr-containing plasmid, yet not the second plasmid, too.

Coexpression can be improved by arranging the marker gene and the foreign gene on one plasmid. By this method, i.a. human interferon β (McCormick et al., Mol. Cell Biol. 4:166, 1984), human interferon γ (Haynes and Weissman, Nucl. Acids Res. 11:687, 1983;) and human interleukin 2 (Onomichi, J. Biochem. 102:123, 1987) have been expressed. The authors used plasmids in which the dhfr gene and the structure gene each have a separate promoter. The authors used a dhfr-deficient hamster cell line CHO as the expression cell line.

Decoupling from the dhfr-deficient cell line CHO for amplification and expression of foreign proteins by using mutant dhfr genes has been attempted by Simonsen et al. and McIvor et al. (supra). Since, however, the mutant dhfr genes tolerate substantially higher MTX concentrations from the beginning, they cannot be amplified over such a great number of steps, as compared to the MTX-sensitive wild type dhfr gene.

Another route of increasing the spectrum of possible expression cell lines has been taken by Walls et al. (Gene 81:139; 1989). Here plasmids have been used, in which the dominant selection marker hygromycin. B phosphotransferase is present in addition to the recessive amplification marker dhfr. The two marker genes and the foreign gene, protein C, each form a separate transcription unit, each of these genes being controlled by a separate promoter. Only one single clone is obtained in this multicistronic expression system, which clone, after hygromycin B (HyB) selection and subsequent dhfr amplification, also expresses recombinant protein C in increasing amounts. Other clones are selectable on HyB, yet they are not dhfr-amplifyable.

Since all systems using the wild type dhfr gene are generally restricted to dhfr-deficient cells, Wernicke and Will (Anal. Biochem. 203:146, 1992) have proposed a cotransfection of three plasmids, each containing the dhfr gene, a dominant marker, and the foreign protein gene. They have, however, found that the foreign gene (human plasminogen activator) is not expressed in increasing amounts by the use of two markers.

Further attempts are being made to improve the expression system by coupling of the two genes, dhfr and foreign gene, even more closely. The two genes are put into a plasmid under the control of only one promoter, wherein on the mRNA formed, the foreign gene followed by the marker gene are found as dicistronic RNA.

According to EP-0 247 145-B1, vectors have been described, in which either a marker gene and a gene for an any desired forein protein, or at least two marker genes and a gene for a foreign protein are transcribed into a dicistronic mRNA. When comparing the translation efficiency of two open reading frames (ORF) in dicistronic RNAs in such constructs, it is found that the translation initiation of the ORF located downstream is more inefficient by about 100 times as compared to the AUG of the first ORF and located upstream (Kaufman et al., EMBO J. 6:187, 1987; Kozak, Mol. Cell. Biol. 7:3438, 1987). In this instance, the ORF located upstream or the ORF not essential to the cell (foreign gene), respectively, may quickly be lost by deletion and DNA rearrangements. Besides, in the Examples of EP-0 247 145-B1, merely the theoretical expression of a foreign gene in CHO cells is described, yet the expression data are missing. By cloning a dominant marker gene in addition to the dhfr gene it has been attempted to widen the spectrum of possible expression cell lines beyond dhfr-deficient CHO cells. On account of the above-discussed deletion and DNA rearrangement phenomena, however, the chance of obtaining a clone that contains all three genes is, very slight indeed.

To keep the coupling of the marker gene with the foreign protein while reducing rearrangements and deletions, attempts have been made to introduce sequence elements between the dicistronic reading frames, to which sequence elements ribosomes can bind internally. These sequence elements are called "Internal Ribosome Entry Sites" (IRES), and they have first been found in the family of picorna viruses. The 5'-untranslated regions (UTR) of polio virus (Pelletier and Sonenberg, Nature 334:320, 1988) and encephalomyocarditis (EMC) virus (Jang et al., J. Virol. 63:1651; 1989) are capable of conferring in cells, the internal binding of the ribosomes and in connection therewith, the translation initiation on mRNAs. By insertion of this sequence between the two open reading frames (foreign protein and selection marker), a coupled, and thus more efficient, translation also of the reading frame located downstream into the dicistronic unit is obtained (Jang, supra), and rearrangements and deletions are avoided (Kaufman, Nucl. Acids Res. 19:4485; 1991). In tricistronic constructions in which the IRES sequence precedes the third cistron, at least the second ORF is deleted. If, however, the IRES precedes the second cistrone, the third ORF is translated only moderately if at all. It is subject to the laws applying to dicistronic constructions without IRES (Jang, supra).

According to DE-A 42 28 458, this system is used to construct a multicistronic expression unit which enables the equimolar expression of the genes positioned in the respective cistrons. Downstream of the IRES sequence, a nucleotide sequence 'Y' is inserted, which is to cause the required equimolar expression of the foreign genes. These expression units are particularly suitable for producing recombinant proteins consisting of two or several protein subunits. As an example of such recombinant proteins, the gene for the "Platelet Derived Growth Factor" consisting of an A- and a B-chain, is expressed with this system.

The use of a fusion protein comprised of two dominant selection markers is described in WO 92/08796. In this instance, a positive selectable gene (hygromycin B-phosphotransferase, hph), and a negative selectable gene (thymidine kinase of the Herpes simplex virus, HSV-1 TK) are fused such that the fusion protein formed lacks the C terminus of the hygromycin B protein and the N terminus of the HSV-1 TK protein. It is shown that the fusion protein is bifunctionally active, and that a host cell expressing this gene gets a dominantly positive selectable and negative selectable phenotype.

An equally bifunctional fusion protein has been constructed by Schwartz et al. (PNAS 88:10416, 1991). The authors fused the HSV-1 TK gene with the bacterial neomycin phosphotransferase (neo) gene in a manner that the HSV-1 TK gene modified at the C terminus was ligated to the start codon of the neo gene in the reading frame.

All strategies hitherto described for optimizing the expression have been developed to produce foreign proteins on a large scale. For producing recombinant vaccines, e.g., large amounts of purified proteins are required. For the treatment of patients suffering from a defective blood coagulation, the availability of large contingents of plasma proteins is enormously important.

Prothrombin could be expressed by Jorgensen et al. (J. Biol. Chem. 262:6729, 1987) in CHO cells without amplification in a concentration of 100 ng of prothrombin/$10^6$ cells within 24 h. After amplification via dhfr, the yields were at 8–11 mU of prothrombin/$10^6$ cells within 24 h. By expressing prothrombin with the vaccinia virus system, an expression of 18–23 mU/$10^6$ cells and day could be attained (Falkner et al., Throm. and Haem. 68:119, 1992).

The cDNA for human factor VIII encodes 2332 amino acids. In the plasma, however, only a fraction of factor VIII is present as a single-chain protein. The dominant factor VIII species is a two-chain molecule comprised of a light chain and of a heavy chain of different length. First attempts at expressing recombinant factor VIII proved to be difficult, since the processing of a protein having such a complicated structure in host cells is carried out very inefficiently. Kaufman et al. (J. Biol. Chem. 263:6352, 1988) were capable of expressing a maximum of 1 U FVIIIc/$10^6$ cells in 24 hours in highly amplified CHO cells (20 $\mu$M or 1 mM MTX, respectively). This value was attained after a 10,000 fold expression increase. Initially, FVIIIc expression was only at the detection limit.

Several set-ups showed that a recombinant factor VIII protein which lacks a major portion of the heavy chain also has coagulative properties which cannot be differentiated from the native molecule (Eaton et al., Biochemistry 25:8343, 1986; Mertens et al., Brit. J. Haematol. 85: 133, 1993). Also in vivo, the B domain is cleaved from the factor VIII by processing. Several groups of authors could even show that the expression of B-domain-deleted factor VIII works substantially better than the expression of the complete factor VIII cDNA (Toole et al. PNAS 83:5939; 1986; Pittman et al., Blood 81:2925, 1993). These references describe an expression of deleted FVIII that is 10–20 times higher than that of FVIIIc. These expression values could, however, only be reached after amplification to 1 $\mu$M or 5 $\mu$m MTX, respectively, and vWF coexpression.

According to U.S. Pat. No. 5,171,844, the factor VIII deletion mutant FVIIIdB928 could be transiently expressed in COS cells at a concentration of 15 mU/ml in 48 h culture.

According to EP-0 351 586-A, an expression plasmid having a factor VIII lacking the amino acids 740 to 1649 under the control of the chicken β-actin promoter is described. If this plasmid is cotransfected with a second plasmid expressing dhfr into CHO cells and subsequently is amplified with 10 nM MTX, the expression of FVIII:C can be increased from approximately 350 mU/$10^6$ cells per day to 1300 mu/$10^6$ cells per day. In comparison to this cotransfection, the transfection with a plasmid containing both, the dhfr gene under the control of the SV40 promoter as well as the cDNA of the deleted factor VIII under the control of the chicken β-actin promoter, shows a considerably lower initial expression of factor VIII than the non-amplified monocistronic plasmid.

Human factor IX was expressed in dhfr-deficient CHO cells with a plasmid that expresses factor IX cDNA and the dhfr gene under the control of the adenovirus major late promoter (Kaufman et al., J. Biol. Chem. 261:9622, 1986). Yet even when amplifying with 20 μM MTX, with up to 188.0 μg/ml of factor IX obtained, only from 0.2 to 4.4% of functional factor IX were produced. The CHO expression system described by Balland et al. obtains only about 30% of functional factor IX with approximately 2 μg of factor IX/ml and 24 hours (Eur. J. Biochem. 172: 565, 1988). WO 86/06408 furthermore describes that non-amplified CHO cells produce only 15 ng factor IX/ml and 24 hours.

Protein C is expressed by Grinell et al. (Adv. Appl. Biotechnol. Series 11:29, 1990) in initial-selected, non-amplified cell clones in a maximum amount of 1.15 μg/$10^6$ cells and day. According to U.S. Pat. No. 4,775,624, 1.8 μg/ml protein C are expressed in CHO DUKX B11 cells. Also in EP-B1 0 266 190 a protein C expression of 1–2 μg/$10^6$ cells in BHK and 293 cells is documented.

The present invention thus has as its object to provide a system which enables an expression of a foreign protein in high yield and purity.

According to the invention, this object is achieved by an expression plasmid containing a dicistronic transcription/translation unit, which unit comprises a sequence for a foreign protein and a sequence for a fusion protein, the fusion protein consisting of at least one amplification marker protein and at least one selection marker protein. When expressing foreign proteins in suitable eukaryotic cells, the expression plasmids according to the invention enable a very high ratio of clones expressing foreign proteins to the total clones, on the one hand, and a surprisingly high initial expression of the foreign proteins, on the other hand.

A preferred embodiment of the plasmid according to the invention additionally comprises an internal ribosome binding site ensuring a more reliable translation of the entire mRNA.

A particularly preferred internal ribosome binding site is the 5'-untranslated region of the encephalomyocarditis virus (ECMV 5'UTR). It enables a particularly good binding of the ribosomes in the internal region of the mRNA, thus positively influencing the translation of an open reading frame located further downstream.

According to a preferred embodiment of the plasmids according to the invention, the encoding sequence for the foreign protein lies 5' and the encoding sequence for the fusion protein lies 3' from the internal ribosome binding site. This arrangement enables a maximum yield of foreign protein, since the gene for the foreign protein is located immediately downstream of the promoter and thus is optimally transcribed.

Preferably, the foreign gene and the sequence for the fusion protein are capable of being transcribed into a dicistronic mRNA, because in this manner the transcription/translation is coupled most closely.

The expression plasmids according to the invention are preferably controlled by a single promoter which is as strong as possible, e.g. by the CMV, the SV40, the human β-actin or similar promoters.

In addition, the plasmids according to the invention may contain an intron, preferably the intron of the SV 40 t antigen, the 16 s/19 s intron or the first intron of the human β-actin gene, and/or a polyadenylation signal, preferably that of the early or of the late transcription unit of SV 40 virus. These components, too, enable optimized expression rates of the foreign protein.

According to a preferred embodiment of the plasmid of the invention, the sequence for the fusion protein comprises two partial sequences, i.e. a highly amplifiable amplification marker gene, preferably the dihydrofolate reductase gene, and a selection marker gene, preferably the hygromycin B phosphotransferase gene.

The dihydrofolate reductase gene/hygromycin B phosphotransferase gene system offers the particular advantage that on account of the tight coupling of the hph and dhfr domains, this fusion protein can be amplified as a dominant marker also in cells having endogenous dhfr gene. This is particularly enabled by the property of a hph amplification potential so that one can speak of a double-dominant selectable and double amplifiable marker protein. Thus, at first a sufficiently high hph amplification can be effected which ensures in the subsequent switching to MTX that the MTX concentration which is selected then, can no longer be compensated by endogenous DHFR.

Preferably, the selection/amplification marker fusion protein is bifunctional, and the sequence encoding the fusion protein is constructed such that the 5'-encoding partial sequence lacks the stop codon and the 3'-encoding partial sequence optionally lacks the start codon. Thereby the fusion protein can be translated easily and efficiently.

In another embodiment of the expression plasmid, the encoding sequences of the two protein portions of the sequence for the fusion protein are separated by a spacer, in particular by a spacer having a length of 15 nucleotides. Preferably, the spacer sequence encodes 5 glycin residues (GGA GGC GGG GGT GGA (SEQ.ID.No.2)) or 5 proline residues (CCA CCC CCG CCT CCA (SEQ.ID.No.1)).

The presence of the spacer protein promotes the functionality of the fusion protein. The activity of the marker proteins in the fusion protein is not reduced relative to the distinct marker proteins.

The amino acid sequences of preferred fusion proteins are listed in the sequence protocol as SEQ.ID.No.3 (fusion protein DHFR/HPH without spacer), SEQ.ID.No.4 (fusion protein DHFR/HPH with glycine spacer) and SEQ.ID.No.5 (fusion protein DHFR/HPH with proline spacer).

Examples of preferred plasmids are the expression plasmids pCMV/EDH-Sp, pCMV/EDHGly and pCMV/EDHPro according to FIG. 4-A.

The expression plasmids according to the invention are particularly suited for the expression of human plasma proteins or of viral proteins and the derivatives or fragments thereof, respectively.

Preferred proteins which can be expressed with the plasmids according to the invention are human prothrombin, human factor VIII, in particular the deletion mutant factor VIIIdB928 of factor VIII that has the largest deletion in the B domain, which still permits the expression of an active factor VIII, human factor IX, human protein C, human serum albumin (HSA) and human von Willebrand factor.

Preferred expression plasmids are:

pCMVFII/EDH-Sp, pCMVFII/EDHGly and pCMVFII/EDHPro (for the expression of prothrombin), pCMVFVIIIc/EDH-Sp, pCMVFVIIIc/EDHGly and pCMVFVIIIc/EDHPro (for the expression of factor VIII), pCMVFVIIIdB928/EDH-Sp, pCMVFVIIIdB928/EDHGly, pCMVFVIIIdB928/EDHPro (for the expression of FVIIIdB928), pCMV-FIX-EDH-Sp, pCMV-FIX-EDHGly and pCMV-FIX-EDHPro (for the expression of factor IX), pCMV-PCwt-EDH-Sp, pCMV-PCwt-EDHPro, pCMV-PCwt-EDHGly, pCMV-PCpt. mut.-EDH-Sp, pCMV-PCpt. mut.-EDHPro and pCMV-PCpt. mut.-EDHGly (for the expression of protein C), pAct-vWF-EDH-Sp, pAct-vWF-EDHPro and pAct-vWF-EDHGly (for the expression of von Willebrand-Faktor).

Expression plasmids which comprise expression cassettes containing the DNA sequences SEQ.ID.No. 6, SEQ.ID.No. 7 or SEQ.ID.No.8 and allowing for an excellent expression particularly of the foreign protein in the transfected cell have proved to be especially advantageous.

According to a further aspect, the present invention relates to a fusion protein comprised of a highly amplifiable amplification marker and a selection marker.

This fusion protein preferably is characterized in that the 5'-encoding gene for the amplification marker lacks the stop codon and the 3'-encoding gene for the selection marker optionally lacks the start codon.

According to a further preferred fusion protein, the amplification marker and the selection marker are separated by a spacer protein which preferably is comprised of at least 5 glycine residues or of at least 5 proline residues.

Examples of such preferred fusion proteins comprise the amino acid sequence SEQ.ID.No. 3, SEQ.ID.No. 4 or SEQ.ID.No.5.

A further aspect of the invention relates to transfected eukaryotic cell lines, preferably selected from the cell lines CHO, 293 or human liver cell lines, such as SK-HEP-1 or Chang liver, transfected with an expression plasmid according to the invention and expressing a foreign protein.

According to another aspect of the invention, the cell line SK-HEP-1 is used as an expression vehicle, in particular for human plasma proteins, such as prothrombin, factor VIII (or factor VIII derivatives, respectively, such as the mutant factor VIII dB928), factor IX, protein C or von Willebrand factor.

Preferably, the transfected eukaryotic cell line expresses human prothrombin, human factor VIII, the deletion mutant dB928 of human factor VIII, human factor IX, human protein C, human serum albumin (HSA) or the human von Willebrand factor, or derivatives or fragments thereof, respectively.

The invention also relates to a method of preparing foreign proteins, characterised in that a eukaryotic cell line is transfected with an expression plasmid of the invention, the clones obtained are isolated by a selection process under the control of the selection marker and preferably simultaneously are amplified, whereupon further amplifications take place under the control of an amplification marker, wherein the foreign protein is expressed and harvested.

In a preferred variant of this method, the selection and initial amplification process is effected by using hygromycin B, and the further amplification is effected by using methotrexate.

In this connection, it has been shown that the combination of the amplification ability and of the dominant selectability of the dhfr gene, on the one hand, and the close connection of the amplification selection marker protein gene with the foreign gene in a dicistronic transcription/translation unit, on the other hand, is of great importance for the yield of foreign proteins.

When optimizing the expression protocol by using the expression plasmids of the invention, the surprising result was obtained that also the hygromycin B phosphotransferase gene is amplifiable. This is contradictory to the general opinion. By slowly increasing the Hy B concentration, i.a. also a co-amplification of the dhfr gene could be obtained which allowed for an adjustment to an MTX concentration already toxic for the endogenous DHFR. It was only then that the amplification proper with MTX was effected via several steps.

This preferred combination of the recessive amplification marker dhfr with the dominant selection marker hph as the fusion protein allows for the amplification of the foreign genes or expression of the foreign proteins, respectively, in any desired cell line. Those cell lines which carry out processing and modification of the proteins completely, are preferred.

CHO, 293 or human liver cell lines, such as SK-HEP-1 and Chang liver (ATCC CCL 13) have proved to be particularly preferred cell lines in the method according to the invention.

In the Examples, both the dhfr-deficient cell line CHO DUKX-B11 (Chasin and Urlaub, PNAS 77:4216, 1980), and the cell lines with endogenous dhfr gene, 293 (ATCC CRL 1573) and SK-HEP-1 (ATCC HTB 52) are used.

According to the invention, liver cell lines are the best suited for the expression of human factor VIII. When using these cell lines, it was found surprisingly, that not only 95% of the factor VIII-transformed cells also express factor VIII, but that also initially a large amount of factor VIII is expressed. Last not least these liver cell lines exhibit an optimum post-translational modification of the recombinant factor VIII.

In particular, of a variety of liver cells tested, the cell line SK-HEP-1 proved to be particularly well suited.

According to the invention, recombinant blood coagulation factors, in particular recombinant human prothrombin, recombinant human factor VIII, recombinant human FVIIIdB928, recombinant human factor IX, recombinant human protein C, human serum albumin (HSA) or recombinant human von Willebrand factor are preferably produced.

Finally, the invention also relates to foreign protein preparations obtainable by the method of the invention and characterized by a particularly high portion of active protein and high purity, in particular also with proteins which must undergo post-translational modification processes to be brought into their active form.

Thus, the present invention particularly relates to preparations of viral proteins or of human plasma proteins, preferably of active human prothrombin, of active human factor VIII, of active human deleted FVIIIdB928, of active human factor IX, of active human protein C, of HSA and of active human von Willebrand factor.

The invention further relates to pharmaceutical compositions comprising one of these preparations according to the invention, in particular plasma protein preparations. These pharmaceutical compositions are obtained from the preparations according to the invention by common methods and are characterized by a particularly good effectiveness or compatibility caused by the efficient production method of the preparations.

By the arrangement according to the invention and by the type of the functional segments (foreign gene, marker fusion protein gene) in the plasmid, the deletions and DNA rearrangements are prevented, on the one hand, while, on the other hand, the functionality of both marker elements and also the expression of diverse proteins in functional form in surprisingly high amounts are ensured. In all the foreign proteins examined, a very high initial expression was already exhibited. As mentioned above, prothrombin, for instance, is expressed in CHO without amplification in an amount of 100 ng/$10^6$ cells in 24 h (Jorgensen et al., supra). In the following Example 1 it is shown that, with the expression plasmid according to the invention, prothrombin could be produced in CHO cells, without amplification, already in an amount of 12 to 15 mU/$10^6$ cells in 24 h (corresponding to 1.2 to 1.5 μg), and in 293 cells even 50 to 55 mU/$10^6$ cells could be produced in 24 h (corresponding to 5 to 5.5 μg). Likewise, with the expression plasmid according to the invention, expression values obtained in the literature for other plasma proteins only after extensive amplification could be dramatically exceeded already at the stage of initial expression. It is particularly pointed out that the expression data stated here do not illustrate the amounts of expressed antigenic protein, but relate to protein amounts found in activity tests.

The invention will now be explained in more detail by way of the drawings as well as by way of the following Examples to which, however, it shall not be restricted.

BRIEF DESCRIPTION OF THE DRAWINGS

FIGS. 5A–C show the amino acid sequence of the fusion proteins: DHFR/HPH without spacer (5A; SEQ.ID.No. 3), DHFR/HPH with glycine spacer (5B, SEQ.ID.No. 4) and DHFR/HPH with proline spacer (5C, SEQ.ID.No. 5), the sequence being stated in the one letter code.

EXAMPLES

Figure 1:
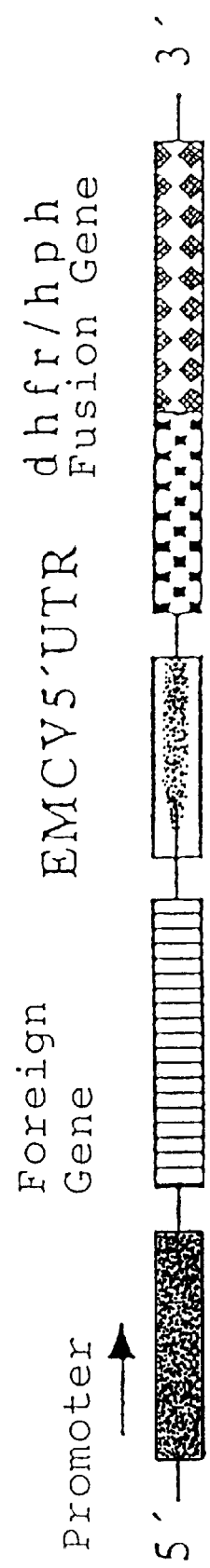
FIG. 1 shows the arrangement of the EDH selection/amplification marker in context with promoter and foreign gene, the arrow indicating the direction of transcription.

In the Examples, the cloning of the expression plasmids is described. The expression of prothrombin is taken as an example to describe transfection, the selection and amplification protocol and the associated control experiments. The verification of the dicistronic mRNA is effected by means of Northern Blots, the amplification of the transcription/translation unit is checked in Southern Blots. Western Blots are used for the precise analysis of the expressed foreign proteins, and finally the recombinant proteins are checked in respect of their activities by means of known activity tests. The activities are given in mUnits (mU) per $10^6$ cells and 24 h. To demonstrate the general usability of the expression plasmids, the expression of the foreign proteins is carried out in various cell lines.

Example 1 describes the cloning of the human factor II with the expression plasmids of the invention in CHO and 293 cells. Cloning and expression of the factor VIII deletion mutant FVIIIdB928 and of the entire factor VIII in 293 and SK-HEP-1 cells is described in Examples 2 and 3. In the further Examples 3 to 6, the expression of the human factors von Willebrand, factor IX, HSA and protein C in the cell lines SK-HEP-1 and 293 cells is described. The cell line SK-HEP-1 is taken as an example of a human liver cell line, yet also other human liver cell lines may be used.

EXAMPLE 1

Cloning of the selection/amplification marker EMCV5'UTR/dhfr/hygromycin-phosphotransferase (EDH) and its application in the expression of factor II.

Construction of the plasmids:

pCMV: pCMVβ (MacGregor and Caskey, Nucleic Acids Res. 17: 2365, 1989, Clontech, Palo Alto, USA). was used as the starting plasmid. It was cleaved with NotI to remove the β-galactosidase gene and subsequently re-ligated. This led to the 3.8 kb plasmid pCMV.

pCMV-MCS: (MCS; multiple cloning site). To remove unnecessary restriction cleavage sites, pCMV was cleaved with SalI and HindIII, filled in with the Klenow fragment of *E. coli* DNA polymerase I (Pol. K.) and re-ligated. pCMV-MCS formed from this reaction. This plasmid contains the "Immediate Early Gene" promoter/enhancer of human CMV and 80 bp of the 5'UTR of the associated gene. 3' there follows a XhoI cleavage site, followed by the SV40 16 S/19 S intron and the SV40 polyadenylation site.

pCMVNco/MCS:pCMV-MCS was opened with XhoI and ligated as new MCS with the complementary oligonucleotides VI/1: 5'-TCG ACC ATG GAC AAG CTT ATC GAT CCC GGG AAT TCG GTA CCG TCG ACC TGC AGG TGC ACG GGC CCA GAT CTG ACT GAC TGA-3' (SEQ.ID.No. 9) and VI/2: 5'-TCG ATC AGT CAG TCA GAT CTG GGC CCG TGC ACC TGC AGG TCG ACG GTA CCG AAT TCC CGG GAT CGA TAA GCT TGT CCA TGG-3' (SEQ.ID.No. 10). This XhoI cleavage site was destroyed, and the vector pCMVNco/MCS (FIG. 3-A) formed. The new MCS had an NcoI-recognition sequence as translation initiation codon, so as to be able to insert and express a foreign gene missing its own ATG start codon.

pCMV/Hy: The hygromycin β-phosphotransferase-(hph)-gene lacking ATG (hph-ATG) was inserted in pCMVNco/MCS. hph-ATG was isolated as the 1.2 kb fragment from the vector pHphO to be obtained from Boehringer Mannheim, isolated as SalI, SmaI fragment and inserted into the SalI- and Pol.K.-treated ApaLI cleavage sites of pCMVNco/MCS. Thus, pCMV/Hy (FIG. 3-B) was formed.

pSVDHFR: The dhfr fragment including the polyadenylating sequence was isolated as the 1500 bp PstI fragment of pASDII (Kaufman and Sharp, Mol. Cell. Biol. 2: 1304, 1982) and inserted in pSVMCS via the PstI cleavage site. pSVMCS was formed from pSVβ (MacGregor and Caskey, supra, Clontech, Palo Alto, USA) by removing the β-galactosidase gene by cleaving with NotI and religation of the remaining vector. By cleaving with XbaI and HindIII, filling in with Pol.K and religation, the MCS 3' of the SV40 polyadenylating sequence was removed. A new MCS was then inserted into the NotI cleavage site. The inserted MCS had the following sequence: 5'-GG CCT AGG GCC CTA GGC CTA CTA GTA CTA AGC TTC TGC AGG TCG ACT CTA GAG GAC CCC GGG GAA TTC AAT CGA TGG CC-3' (SEQ.ID.No. 11).

pTA/ED(-TAA) (FIG. 2): The cassette consisting of the 5' untranslated region of the encephalomyocarditis virus (EMCV5'UTR) and the dhfr fragment lacking the stop codon TAA (-TAA) was subcloned into the vector PCR™ (Invitrogen, San Diego, USA). The production of the EMCV5'UTR/dhfr(-TAA) fragment was effected by means of polymerase chain reaction (PCR). The 500 bp EMCV5'UTR-fragment was isolated from pTKemc-PT2 (WO 91/11519) by PCR with the primers #640, 5'-ACC CCC GGG GGT ACC ATA TTG CCG TCT TTT GG-3' (SEQ.ID.No. 12) and #642, 5'-GGA ATT CCC ATG GTA TTA TCG TGT TTT TC-3' (SEQ.ID.No. 13).

The 560 bp dhfr fragment was isolated from pSVDHFR by means of PCR with the primers #634, 5'-GGA AGC TTG GCC ATG GTT CGA CCA TTG AAC TGC-3' (SEQ.ID.No. 14) and #698, 5'-GGT CAA GCT TTT CTT CTC GTA GAC TTC AAA CTT ATA CT-3' (SEQ.ID.No. 15).

Figure 4A:
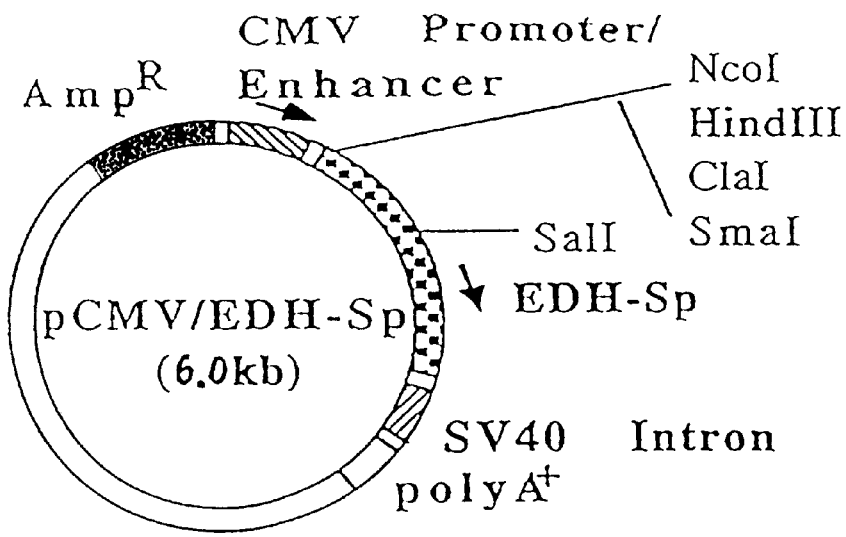
FIGS. 4(A–B) show the structure of the plasmids pCMV/EDH-Sp (4A) and pCMVFII/EDH-Sp (4B).
Figure 4B:
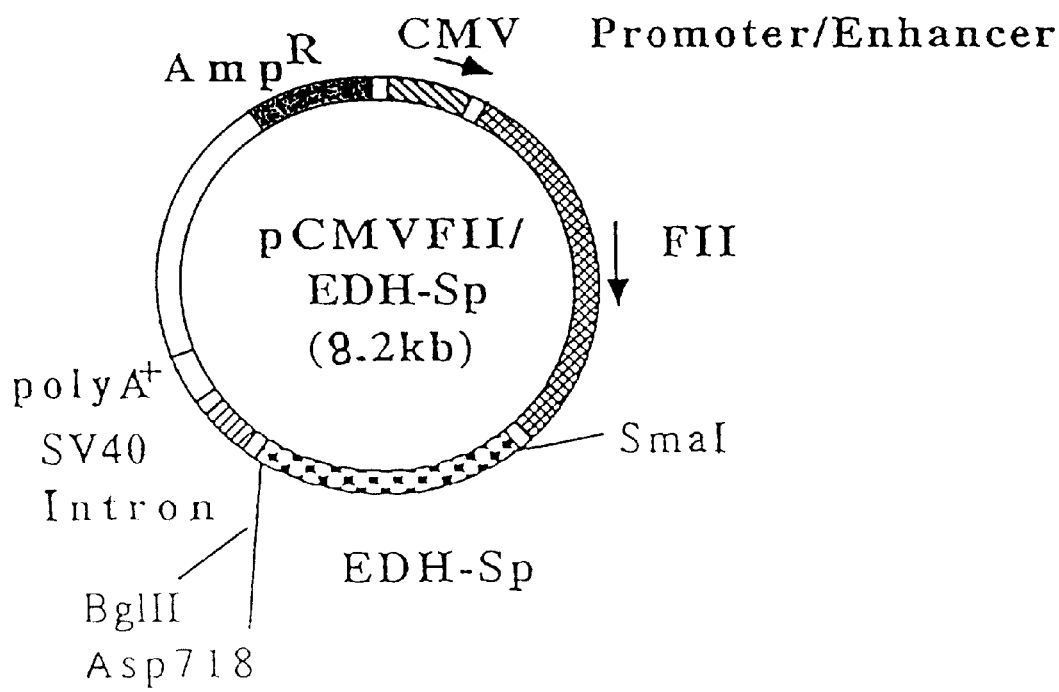

The EMCV5'UTR and dhfr fragments obtained by PCR amplification were isolated according to the gel electrophoretic separation from "low melting point agarose" (LMA). The two fragments were each cleaved with NcoI and ligated. From the ligation product, another PCR amplification was set up with the flanking primers, i.e. with the primers #640 and #698 (cf. above). The resulting 1050bp fragment was inserted in the vector PCR™ (Invitrogen, San Diego, USA). This led to plasmid pTA/ED(-TAA).

pCMV/EDH-Sp: Into the vector pCMV/Hy opened with SamI and SalI, the SmaI SalI fragment EMCV5'UTR/dhfr (-TAA) from pTA/ED(-TAA) was inserted. This led to the construct pCMV/EDH-Sp (FIG. 4A).

pCMV/EDHGly: A spacer was inserted into the singular SalI cleavage site between dhfr and hph gene. The spacer was comprised of the complementary oligonucleotides #1077 (5'-TCG ATT ACG TAC TGG AGG CGG GGG TGG AAA-3'; SEQ.ID.No. 16) and #1078 (5'-TCG ATT TCC ACC CCC GCC TCC AGT ACG TAA-3'; SEQ.ID.No. 17), had a new SnaBI cleavage site and encoded five glycine residues. The link between dhfr and hph thus had the sequence: 5'-GT CGA TTA CGT ACT GGA GGC GGG GGT GGA AAT CGA CGG ATC CC-3' (SEQ.ID.No. 18).

pCMV/EDHPro: The spacer from pCMV/EDHGly was inserted in reverse orientation into the singular SalI cleavage site between the dhfr and hph genes. Thus, it encoded five proline residues here, the transition between dhfr and hph having the following sequence: 5'-GT CGA TTT CCA CCC CCG CCT CCA GTA CGT AAT CGA CGG ATC CC-3' (SEQ.ID.No. 19).

pCMVFII/EDH-Sp (FIG. 4B): The factor II cDNA was isolated from pTKemc-PT2 as the 2 kb fragment (WO 91/11519) by cleaving with NcoI partially and with SmaI completely. This fragment was inserted into the vector pCMV/EDH-Sp, after being cleaved with NcoI partially and with SmaI completely.

pCMVFII/EDHGly: Factor II cDNA was isolated from pTKemc-PT2 as the 2 kb fragment (WO 91/11519) by cleaving with NcoI partially and with SmaI completely. This fragment was inserted into the vector pCMV/EDHgly, which also had been cleaved with NcoI partially and with SmaI completely.

pCMVFII/EDHPro: The factor II-cDNA was isolated from pTKemc-PT2 as the 2 kb fragment (WO 91/11519) by cleaving with NcoI partially and with SmaI completely. This fragment was inserted into the vector pCMV/EDHPro, which had also been cleaved partially with NcoI and completely with SmaI.

Production of the permanent cell lines:

Initial selection: CHO- (Urlaub and Chasin 1980, PNAS 77:4216–4220) and 293 cells (ATCC CRL 1573) were obtained from the American Type Culture Collection (Rockville, Md.). Both cell lines were transfected with the constructs pCMVFII/EDH-Sp, pCMVFII/EDHGly and pCMVFII/EDHPro according to Graham and von der Eb, Virology 52: 456, 1973. CHO cells were subjected to DHFR selection, hygromycin B selection and simultaneous hygromycin B (HyB) and DHFR selections. 293 cells were exposed to hygromycin B selection. After 10–20 days, resistant colonies were isolated and tested for factor II (FII) expression.

DHFR selection medium: DMEM/HAMs F12 lacking glycine, thymidine and hypoxanthine, but containing 10% dialysed fetal calf serum, 10 IU/ml penicillin, 100 μg/ml streptomycin (Gibco 043-05140H), L-glutamine (Gibco 043-05030H).

Hygromycin B selection medium: DMEM/HAMs F12, 10% fetal calf serum, 10 IU/ml penicillin, 100 μg/ml streptomycin (Gibco 043-05140H), L-glutamine (Gibco 043-05030H), 10 μg/ml each of adenosine, thymidine and deoxyadenosine (Sigma), 200 μg hygromycin B (Calbiochem)/ml.

Gene amplification: The amplification via hph was effected by means of hygromycin B (HyB) starting with 200 μg HyB/ml. To minimize the chance of rearrangements or deletions caused by too high concentrations of HyB, the HyB concentration was only doubled per amplification step. With CHO cells, amplification by means of DHFR started at 10 nM methotrexate (MTX), and continued by doubling the MTX concentration per stage. Amplification of 293 cells was set up starting at 100 nM of MTX. The resistant cell clones forming in each amplification step were isolated as single colonies and investigated for factor II expression.

Determination of factor II activity: The cell clones to be tested and expressing factor II were incubated for 24 hours with serum-free DHFR selection medium, supplemented with 5 μg/ml vitamin K1. The coagulation activity was determined with a coagulometer KC4A (Amelung GmbH, Federal Republic of Germany) according to a modified prothrombin-time-method (Falkner et al. 1992).

Protein detection by means of Western Blot analyses: Western Blots were carried out according to Towbin et al., PNAS 76: 4350, 1979. A rabbit anti-prothrombin antibody (Dakopatts, Denmark) in a dilution of 1:100 was used as the first antibody. A goat-anti-rabbit antibody (BioRad, CA, USA) in a dilution of 1:7500 was used as the second antibody, which was conjugated with alkaline phosphatase. Detection by staining was performed according to standard methods with the Protoblot system of Promega.

Examination of DNA and RNA structures: Preparation of cellular DNA was according to Gross-Bellard et al., Eur. J. Biochem. 36: 32, 1973, Southern Blot analyses according to Southern (J. Mol. Biol. 98: 503, 1975) and according to Sambrook et al., Molecular Cloning, A Laboratory Manual, Second Edition, Cold Spring Harbor Laboratory Press, 1989, respectively. The restriction enzymes necessary for cleaving the cellular DNA were obtained from Boehringer Mannheim, Federal Republic of Germany. The hybridizing probes factor II, dhfr and hph were prepared from plasmids pCMVFII/EDHPro, pSVDHFR and pCMV/Hy.

Isolation of the mRNA was effected with the materials and according to the protocols provided by Invitrogen, USA ("Fast Track"), Northern Blot analyses were carried out according to Sambrook et al., supra. RT-PCR analyses were carried out with the materials provided by Perkin Elmer Cetus, USA (The Reverse Transcriptase RNA PCR Kit", #N808-0069) according to Kwok, PCR Protocols. A Guide to Methods and Applications. Academic Press, Inc., San Diego, Calif. 1990, and Myers et al., Biochemistry 30: 7661, 1991, respectively, 2 μg mRNA being used for each reaction. As the primers, upstream primer #1489 (binds 3' in the factor II cDNA), 5' GGA AAT ATG GCT TCT ACA CAC ATG TGT TCC GCC TGA A 3' (SEQ.ID.No. 20) and, as the downstream primer #1490 (binds 5' in dhfr gene), 5' TCC GTT CTT GCC AAT CCC CAT ATT TTG GGA CAC GGC G 3' (SEQ.ID.No. 21) were utilized.

Construction of the selection/amplification marker EMCV5'UTR/dhfr/hygromycin phosphotransferase (EDH): Most commonly, the CHO cell expression system involves DHFR selection and subsequent methotrexate (MTX) amplification, respectively, and is dependent on the availability of DHFR deficient cell lines, such as CHO DUKX B11 (Urlaub and Chasin, supra). Since, however, CHO cells are not suitable for the expression of all proteins desired, attempts were made to efficiently exploit other cell lines as expression systems. With this aim in mind, the EDH marker has been constructed. Its main use is in cells which have an endogenously functional dhfr gene, since in such cell lines the selection and gene amplification, respectively, by DHFR and MTX, respectively, can be carried out only insufficiently.

This EDH marker is a bifunctional fusion protein composed of the dihydrofolate reductase (dhfr) gene and the hygromycin phospotransferase (hph) gene. The hph gene was chosen because it constitutes a very good dominant selection marker, and the dhfr gene because it constitutes the best though recessive amplification marker.

Since it could not be excluded that the two fused enzymatic protein units might influence or even hamper each other in respect of their activities on account of their closeness in space, it has been attempted to prevent this by inserting a so-called "spacer" between the two fusion protein portions. This spacer is a short oligonucleotide, which encodes five glycine residues in one orientation ("glycine spacer", Gly), and five proline residues in reverse orientation ("proline spacer", Pro). By the chosen arrangement of the foreign gene to be expressed and the fusion marker gene it should be possible to form a dicistronic RNA. This could be achieved by adding to the 5' end of the fusion marker on DNA level a sequence functioning as internal ribosome entry site (IRES). In this instance, the IRES of the encephalomyocarditis virus (EMCV) was used. It is in the 5' untranslated region (5'UTR) of the EMCV, thus being called EMCV5'UTR. The resulting gene cassette consisting of EMCV5'UTR/-dhfr/hph (EDH) was arranged 3' to the foreign gene to be expressed, which led to the configuration of promoter, foreign gene and EDH cassette illustrated in FIG. 1.

Figure 2:
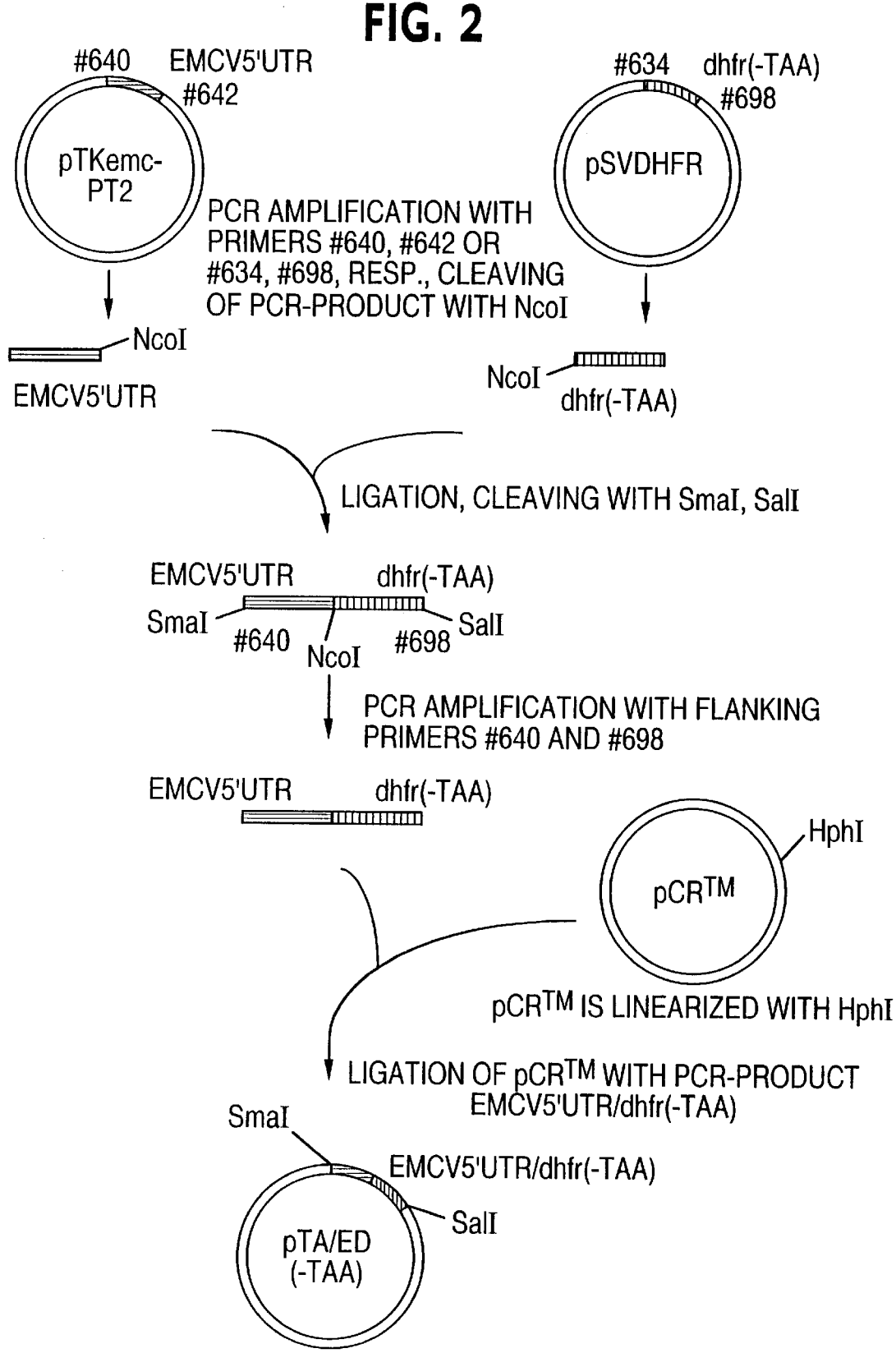
FIG. 2 shows the construction of the ED cassette and subcloning in pCRTM.
Figure 3A:
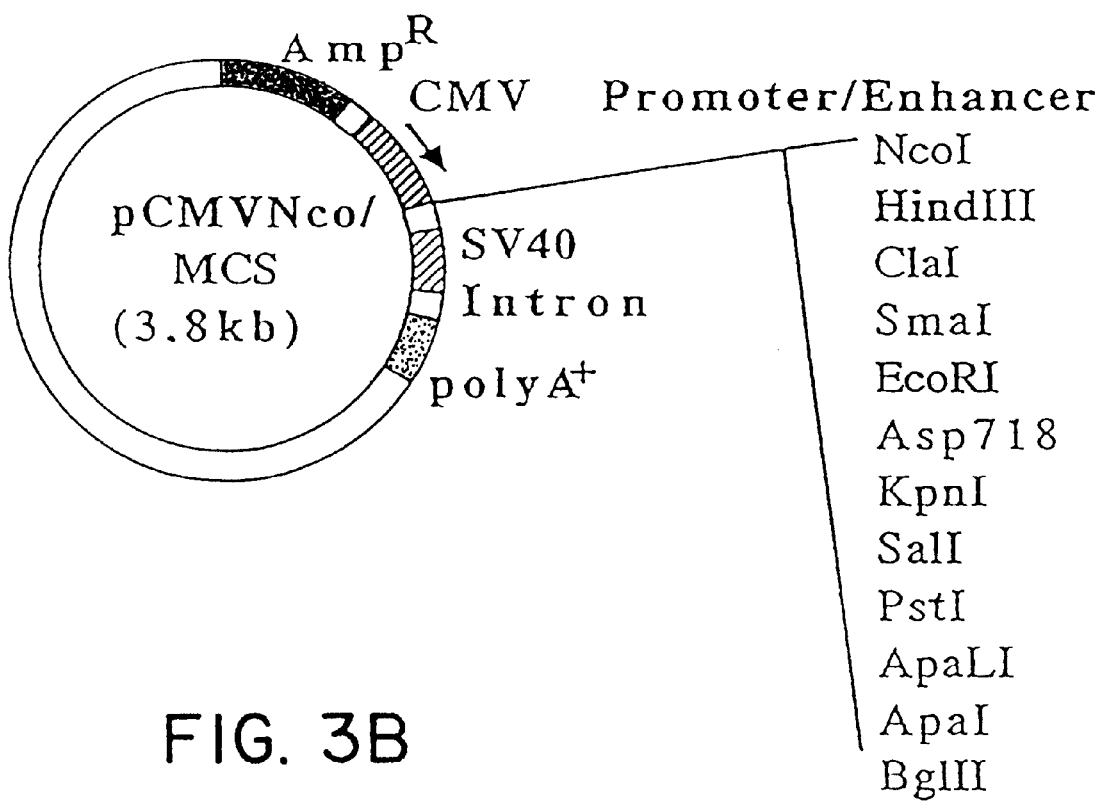
FIGS. 3A–3B show the structure of the plasmids pCMVNco/MCS (3A) and pCMV/Hy (3B).
Figure 3B:
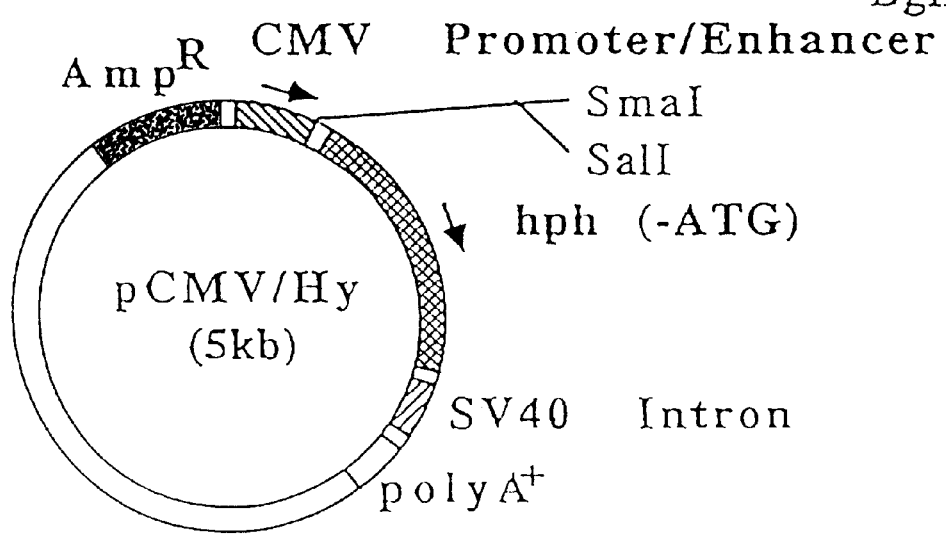

For the fusion protein of the EDH selection/amplification marker, the EMCV5'UTR/dhfr (ED) cassette was cloned via PCR. By means of PCR, the EMCV5'UTR fragment was isolated from the plasmid pTKemc-PT2 (WO 91/11519) and the dhfr fragment (lacking the stop codon TAA) was isolated from plasmid pSVDHFR. The two amplification products were cleaved with NcoI, ligated, and the ligation product was again amplified by means of PCR and subsequently subcloned into the vector PCR™ (Invitrogen, San Diego, USA). The construction scheme is illustrated in FIG. 2. From the resulting plasmid pTA/ED (-TAA), the cassette EMCV5'UTR/dhfr (-TAA) was isolated and inserted into plasmid pCMV/Hy (FIG. 3-B). Plasmid pCMV/Hy already had the hygromycin phosphotransferase gene (from pHphO, Boehringer Mannheim, Federal Republic of Germany) lacking the start codon (hph-ATG). This procedure led to the 2,2 kb gene cassette EDH in the form of the construct pCMV/EDH-Sp (FIG. 4-A). In this plasmid, the dhfr gene was present immediately fused to the hph gene. To prevent a potential hampering of the two components DHFR and hygromycin phosphotransferase (HPH) on protein level, a short oligonucleotide was inserted as spacer between the two genes. This resulted in the three variants of the selection/amplification marker, EDH-Sp, EDHGly, and EDHPro. In FIG. 4-A, the expression plasmid pCMV/EDH-Sp is illustrated representatively, the two other expression plasmids were termed pCMV/EDHGly and pCMV/EDHPro, respectively.

Into these three starting vectors, the factor II cDNA was inserted as gene of interest as the 2.2 kb NcoI-SmaI fragment from pTKemc-PT2 (WO 91/11519), thus forming the expression plasmids pCMVFII/EDH-Sp, pCMVFII/EDHGly and pCMVFII/EDHPro. pCMVFII/EDH-Sp is representatively illustrated in FIG. 4-B.

The amino acid sequences of the fusion proteins DHFR/HPH-Sp, DHFR/HPHGly and DHFR/HPHPro are illustrated in FIGS. 5-A, B and C.

Examination of the functional characteristics of the EDH selection/amplification marker in transfected cells: The three constructs pCMVFII/EDH-Sp, pCMVFII/EDHGly and pCMVFII/EDHPro were examined with regard to their selection and amplification properties. For this purpose, they were transfected into CHO and 293 cells. In DHFR deficient CHO cells (Urlaub and Chasin, supra), separate as well as concomitant functioning of the two fusion protein components DHFR and HPH were tested. The transfected 293 cells as representatives of a DHFR positive cell line were examined in respect of the function of the HPH component, by selecting them with the antibiotic hygromycin B (HyB). The results of DHFR and HPH initial selection are summarized in Table 1.

TABLE 1

|  | CHO-cells/ EDH-system mUnits (μg)/ 10⁶ cells | CHO-cotransfection (Jorgensen et al., 1987) mUnits (μg) 10⁶ cells | 293 cells mUnits (μg) 10⁶ cells |
| --- | --- | --- | --- |
| Initial selection | 12–15 (1.2–1.5) | (0.1) | 50–55 (5–5.5) |
| Amplification 100 nM MTX | / | / | 100–150 (10–15) |
| 150 nM MTX | 150–160 (15–16) | / | / |
| 1000 nM MTX | / | 8–11 (1.3–1.6) | / |

They show that CHO cells initially express between 12–15 mU factor II/10⁶ cells and 24 hours, with 293 cells values of up to 55 mU factor II/10⁶ cells and 24 hours could be detected. The expression system according to the invention thus shows an unexpectedly high expression of factor II in CHO cells after initial selection. However, this high expression of factor II could be further increased when using the cell line 293.

The cell clones resulting from the initial selection were investigated for the amplification ability of the DHFR and HPH components of the EDH marker. The results of this are also summarized in Table 1. Here, too, it could be shown that already at 100 nM MTX, 293 cells express the same amount of factor II as compared to CHO cells growing on 150 nM MTX.

The formation of dicistronic RNA and the functioning of the EDH marker were examined by way of the expression of factor II. The initially selected transfected CHO and 293 cell clones exhibited the presence of dicistronic RNAs in the Northern Blot analysis and in the RT (reverse transcriptase) PCR.

Both, the initially selected and the amplified CHO and 293 cell clones were examined in respect of their genomic structure by means of Southern Blot analysis. The initially selected cell clones exhibited a copy number in the range of 1–5 gene copies/cell. Upon amplification via the HPH component of the EDH marker, starting from 200 μg HyB/ml up to 3000 μg HyB/ml, a moderate gene amplification could be found (cf. also Example 2).

Figure 6:
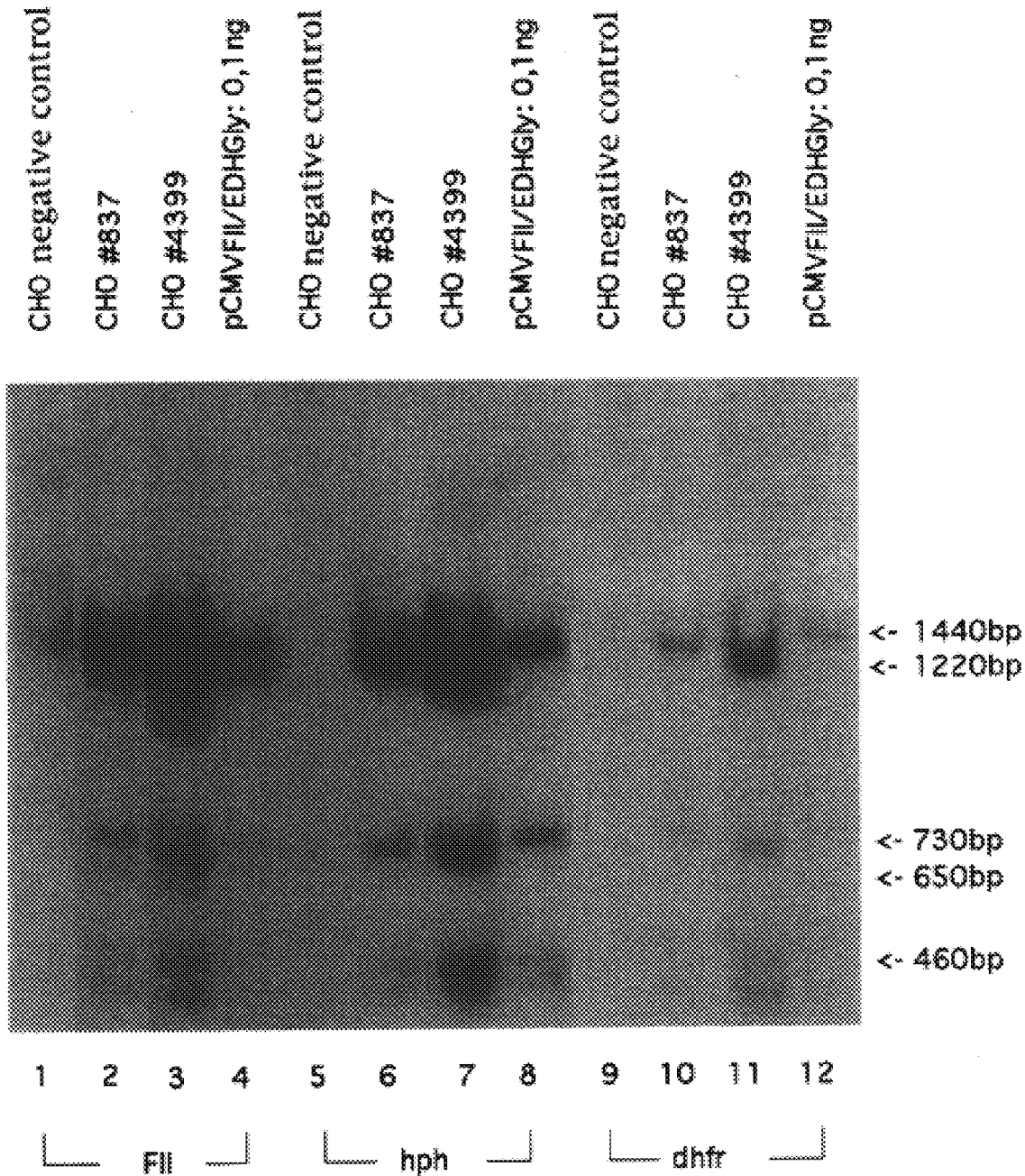
FIG. 6 shows the Southern Blot analysis of genomic DNA of the CHO cell clones #837 (transfected with pCMVFII/EDH-Sp, DHFR initial selection) and #4399 (subclone of #837, amplified on 40 nM MTX).

The amplification via the DHFR component of the EDH marker was examined by exposing transfected CHO cells, starting from 10 nM MTX, to a successively increased MTX concentration up to 40 nM. Despite this modest increase in the MTX concentration, gene amplification could clearly be proven (FIG. 6). This becomes clear when the signal intensities of the DHFR initially selected CHO clone #837 are compared to those of the CHO clone #4399, derived therefrom, amplified to 40 nM MTX. This effect could be proven both when hybridizing with a factor II specific probe (#837 in lane 2 and #4399 in lane 3) and in a hph (#837 in lane 6 and #4399 in lane 7) and dhfr (#837 in lane 10 and #4399 in lane 11) specific probe. Lanes 1, 5 and 9 each represent the negative controls from non-transfected CHO cells. In lanes 4, 8 and 12 the reference plasmid pCMVFII/EDHGly was applied.

The effect of the gene amplification via the DHFR component of the EDH marker could be determined both in initially DHFR-selected CHO cells (FIG. 6) and in initially HyB-selected cells.

Figure 7:
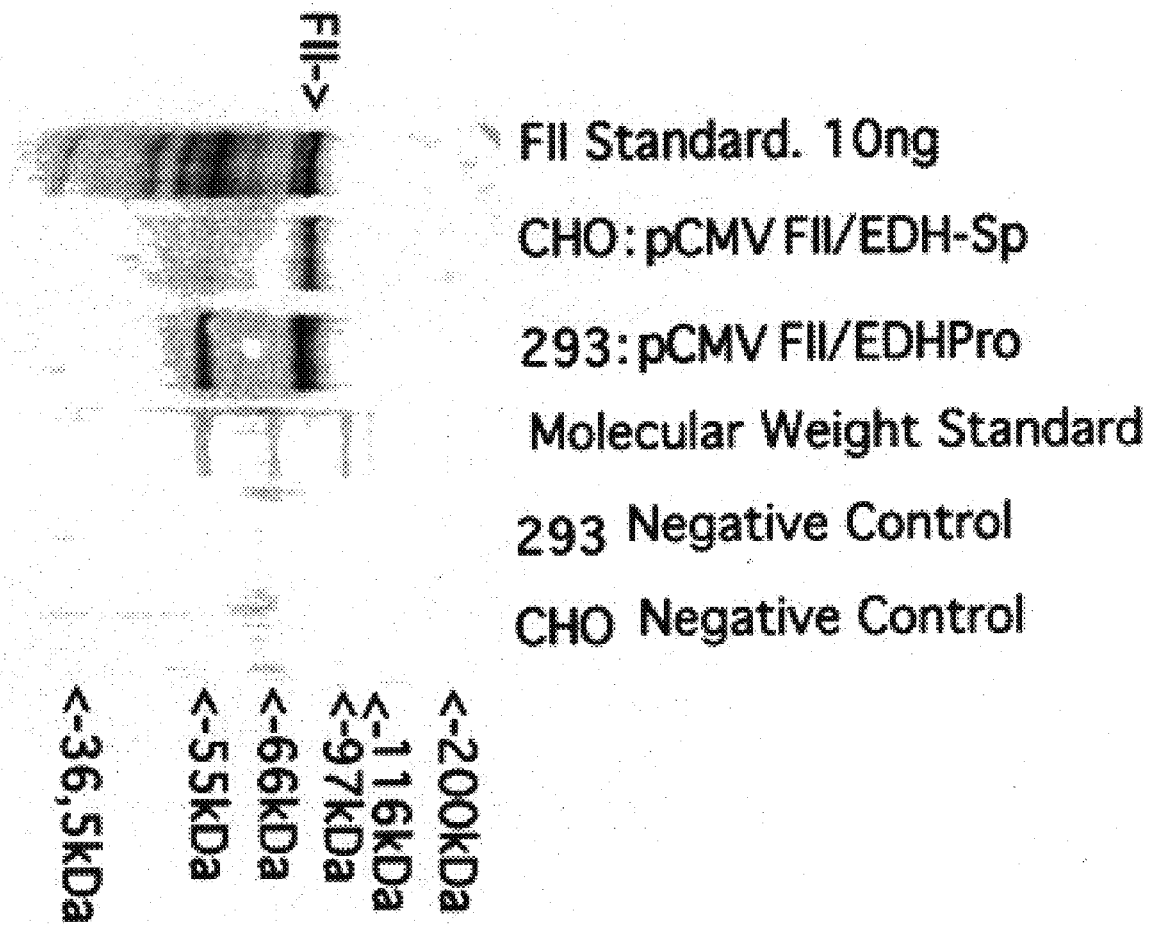
FIG. 7 shows the Western Blot analysis of 293 and CHO cell clones, respectively, transfected with the plasmid pCMVFII/EDHPro and pCMVFII/EDH-Sp., respectively.

Expression of factor II: The identity of the expressed factor II with its plasmatic analogue was ascertained by Western Blot analyses (FIG. 7). The numbers indicated at the margin are the molecular weights in kDa. The factor II-specific band is marked with an arrow.

The DHFR-mediated amplification also led to an increase in the factor II expression. Initially, the expression of factor II in CHO cells was 12–15 mU/10⁶ cells and 24 h (corresponding to at least 1.2–1.5 μg factor II/10⁶ cells and 24 h). With the system described herein, it was also possible to obtain an increase of at least one factor of 10 as compared to the literature. With 293 cells, initial values of 50–55 mU (corresponding to at least 5–5.5 μg) of factor II/10⁶ cells and 24 h were obtained, thus expressing significantly more factor II than initially selected CHO cells.

At 150 nM of methotrexate (MTX), the amplification, in CHO cells resulted in expressions in the range of 150–160 mU (corresponding to at least 15–16 μg) of factor II)/10⁶ cells and 24 h. Thus, despite this relatively low amplification level, markedly higher values could be obtained as compared to the literature. The data of at least 15–16 μg factor II at 150 nM MTX described here are already activity values so that the expression increase with the system described here was remarkable. With the method described by Jorgensen, only a tenth of the expression values of the invention could be obtained, in spite of a 7-fold higher MTX concentration level. Moreover it must be emphasized that, surpassing 150 nM MTX, a large MTX amplification potential is still available.

The expression values attainable in CHO and 293 cells with the EDH marker expression system described herein and with the conventional system of CHO. cotransfection (Jorgensen et al., supra) are illustrated in comparison in Table 1.

EXAMPLE 2

Expression of complete factor VIII (FVIIIc) and of the deletion mutant FVIIIdB928 in transfected 293 and SK-HEP-1 cells.

Figure 8A:
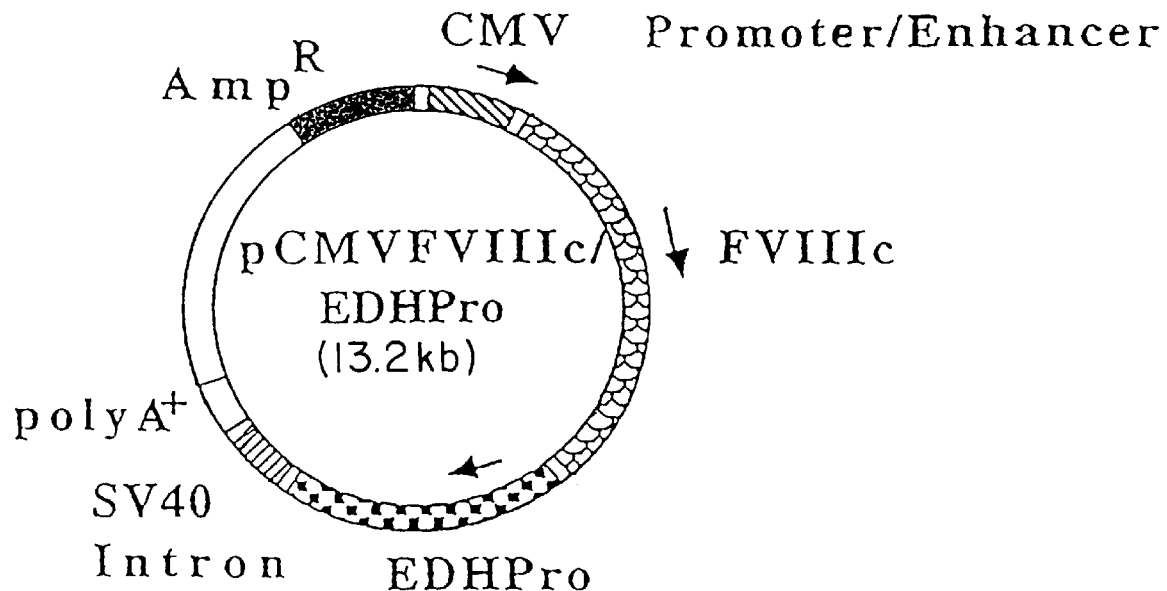
FIGS. 8A–8B shows the structure of the plasmids pCMVFVIIIc/EDHPro (8A) and pCMVFVIIIdB928/EDHPro (8B)
Figure 8B:
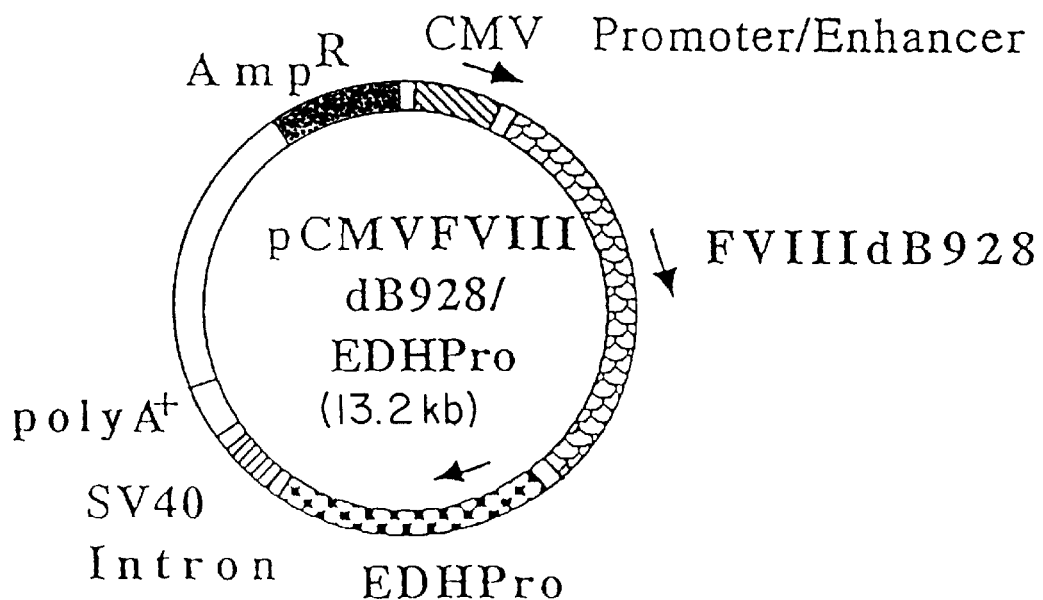

Construction of plasmids:

pCMVFVIIIc/EDHPro (FIG. 8-A): The full-length factor VIII cDNA was constructed by Leyte et al., Biochem. J. 263: 187, 1989. The 7.2 Kb factor VIII cDNA was inserted into the SmaI cleavage site of pCMV/EDHPro as a fragment with blunt ends (cf. Example 1). This resulted in the expression plasmid pCMVFVIIIc/EDHPro.

pCMVFVIIIdB928/EDHPro (FIG. 8-B): The deletion of the factor VIII B domain is described in Leyte et al., J. Biol. Chem. 266: 740, 1991. The 4.4 kb FVIIIdB928 cDNA fragment was inserted into the SmaI cleavage site of pCMV/EDHPro as fragment with blunt ends (cf. Example 1).

Preparation of permanent cell lines: initial selection: 293 cells (ATCC CRL 1573) were obtained from the American Type Culture Collection (Rockville, Md., USA), transfected with the constructs pCMVFVIIIdB928/EDHPro and pCMVFVIIIc/EDHPro, respectively, according to Graham and van der Eb, supra, and subjected to HyB selection (cf. Example 1). After 10–20 days, the resisten colonies were isolated and tested for factor VIII expression.

SK-HEP-1 cells (ATCC HTB 52) were obtained from the American Type Culture Collection (Rockville, Md., USA) and transfected with the constructs pCMVFVIIIdB928/EDHPro and pCMVFVIIIc/EDHPro, respectively. The transfection was performed according to Neumann et al., EMBO J. 1: 841, 1982, in modified form. Therein, 1–3×10⁷ cells were used for an electroporation set up, wherein the pulse was carried out by means of a BioRad Gene Pulser™ (BioRad, CA, USA) at 1000 V, 25 μF, 200 Ohm. Following the pulse, the cells were taken up in medium and transferred in HyB selection medium (cf. Example 1) 48 hours after the pulse. After 10–20 days, the resistant colonies were isolated and tested for factor VIII expression.

Gene amplification: The amplification by means of hygromycin B (HyB) was effected by doubling the HyB concentration in each step, starting at 200 μg HyB/ml (cf. Example 1). Amplification by means of DHFR with 293 and SK-HEP-1 cells was effected by doubling the MTX concentration in each step, starting at 100 nM methotrexate (MTX). The resistant cell clones forming in each amplification step were isolated and tested for factor VIII expression.

Activity determination of factor VIII: All the activity tests were effected with the materials ("COATEST VIII:C/4") and according to the protocol of Chromogenix AB, Sweden, and with the "Immunochrom VIII:C" kit of Immuno, Austria.

Protein detection by means of Western Blot analyses: Western Blots were carried out according to Towbin et al. (supra). As the first antibody, a mixture of the monoclonal anti-factor VIII antibodies CLB CagA, CLB Cag 9 and CLB Cag 117 were used (all three, Stel at al., Blood 63: 1408, 1983). As the second antibody, a goat-anti-mouse antibody (BioRad, Ca, USA) in a dilution of 1:7500 was used, which was conjugated with alkaline phosphatase. Detection by staining was carried out according to standard methods with the Protoblot system of Promega.

Examinations of the DNA and RNA structure: The preparations of DNA and RNA were effected as described in Example 1. For hybridizing Southern and Northern Blots, respectively, factor VIII, dhfr and hph, fragments were isolated from the respective plasmids (i.e. from pCMVFVIIIc/EDHPro, pSVDHFR and pCMV/Hy).

Hitherto, for the expression of factor VIII particularly CHO cells have been examined (Kaufman et al., J. Biol. Chem. 263: 6352, 1988; Pittman et al., Blood 81: 2925, 1993). The DHFR-deficient CHO cells were interesting insofar as they can be selected easily via DHFR and amplified highly with MTX. Yet the decisive disadvantage in the context of utilization of CHO cells resides in the fact that they express merely very slight amounts of factor VIII, and at initial selection, no factor VIII can be detected. Thus, the isolation of factor VIII-expressing CHO cell lines requires high amplification. This involves a very high Screening expenditure, since the amplification must occur "blind", i.e. without previous testing of initially selected cell clones. Moreover, it proved to be difficult to establish stable foreign protein-expressing CHO cell lines, since double minute chromosomes occur frequently (Schimke et al., Cold Spring Harbor Symp. Quant. Biol. 45, 1981; Kaufman et al., Mol. Cell. Biol. 3: 699, 1983). Also for this reason, with the CHO cell system a stable foreign protein expression can be obtained only by frequent and laboursome sub-cloning of the cell clones examined, which, however, is the more laboursome, the higher the respective cell clones are amplified.

For these reasons, in addition to CHO cells, other though DHFR-positive cell lines should be investigated for their factor VIII expression ability. Preferably, human cell lines should be used so as to exclude possible species-dependent changes of the post-translational modifications required. In order to enable an efficient selection of these DHFR-positive cell lines, on the one hand, and to enable their amplification via dhfr, on the other hand, the EDHPro-selection/amplification marker was used. As the cell lines, 293 and SK-HEP-1 cells were used in comparison. Since factor VIII is endogenously synthesized particularly in the liver, SK-HEP-1 cells were used as representatives of human liver cells.

So far, in the literature there have not been any references about the cell line SK-HEP-1 as expression vehicle. Cell line 293 has already been used for the expression of protein C (Walls et al., 1989), and has been proven to be useful for the expression of factor II (cf. Example 1). Yet neither cell line has been investigated or described for the expression of factor VIII.

Although the complete factor VIII cDNA (FVIIIc) has also been utilized, the emphasis had been on the expression of the factor VIII mutant (FVIIIdB928) which had the entire B domain deleted (Leyte et al., J. Biol. Chem. 266: 740, 1991).

The construction of the EDH selection/amplification marker was effected as described in Example 1. The expression plasmid pCMVFVIIIc/EDHPro (FIG. 8-A) was formed by inserting the complete factor VIII cDNA into pCMV/EDHPro as a fragment with blunt ends.

pCMVFVIIIdB928/EDHPro was formed analogously.

Preparation and analysis of pCMVFVIII/EDHPro-transfected cell lines: The cell lines 293 and SK-HEP-1, respectively, were transfected with the constructs pCMVFVIIIdB928/EDHPro and with pCMVFVIIIdB928/EDHPro and with pCMVFVIIIc/EDHPro, respectively, and subjected to HyB selection. The resulting cell clones were examined for their cRNA structure as in Example 1. The RNAs formed were dicistronic. The estimate of the gene copy number present was carried out by means of Southern Blot analysis and was in the range of 1–2 in the case of the 293 cells examined, and in the range of 5–10 in the case of the SK-HEP-1 cells examined.

Figure 10:
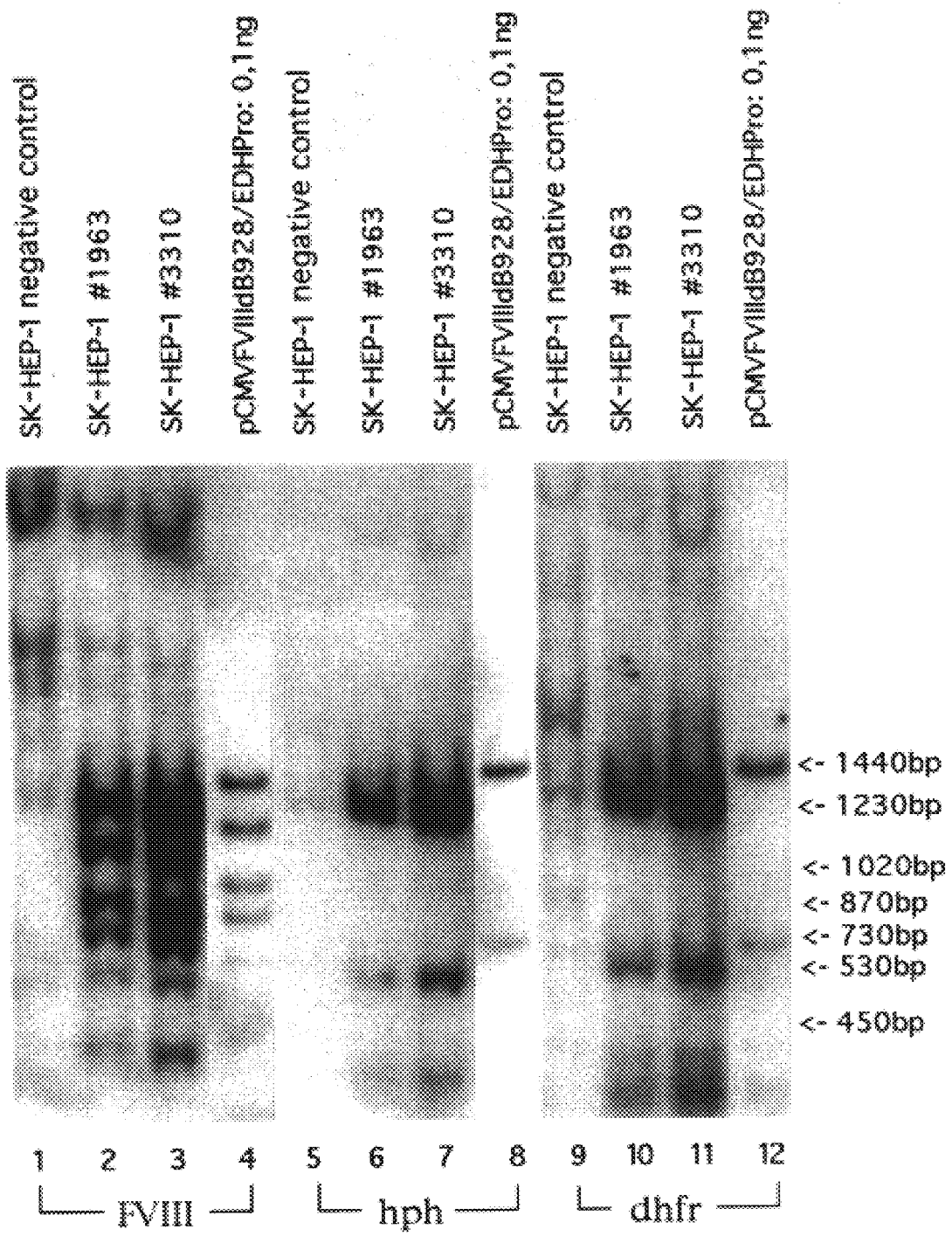
FIG. 10 shows the Southern Blot analysis of genomic DNA of SK-HEP-1 cell clones #1963 (400 μg HyB/ml) and #3310 (1500 μg HyB/ml), clone #3310 being derived from #1963.

The amplification of the transfected, FVIIIdB928-expressing SK-HEP-1 cells via hph from 200 μg HyB/ml to 1500 μg HyB/ml clearly showed the effect of the gene amplification, as is illustrated in FIG. 10. The TaqI-cleaved cellular DNA of the initially selected cell clones #1963 was compared to the cell clone #3310 that had been amplified on 1500 μg HyB/ml and had been derived therefrom. After all the hybridizations with a probe specific for factor VIII (lanes 1–4), dhfr (lanes 9–12) and hph (lanes 5–8), clone #3310 exhibited an amplification of the signal intensities as compared to #1963. The internal standard is given by the reaction of the endogenous factor VIII bands. By comparing these endogenous factor VIII bands of the SK-HEP-1 negative control (lane 1) with those of the clones #1963 (lane 2) and #3310 (lane 3), also the estimate of the factor VIII gene copies present and the adjustment of the applied DNA amount, respectively, are possible. Lanes 4, 8 and 12 each show the reference plasmid pCMVFVIIIdB928/EDHPro.

100 nM MTX was found to be the optimum MTX concentration for the switch from HyB selection to DHFR amplification. The subsequent amplification was effected according to the principle of the common DHFR amplification (cf. Example 1).

Cell clone #5235 derived from subcloning of SK-HEP-1 clone #1963 has been deposited with the ECACC and has received the provisional official identification number 94 092111.

Figure 9:
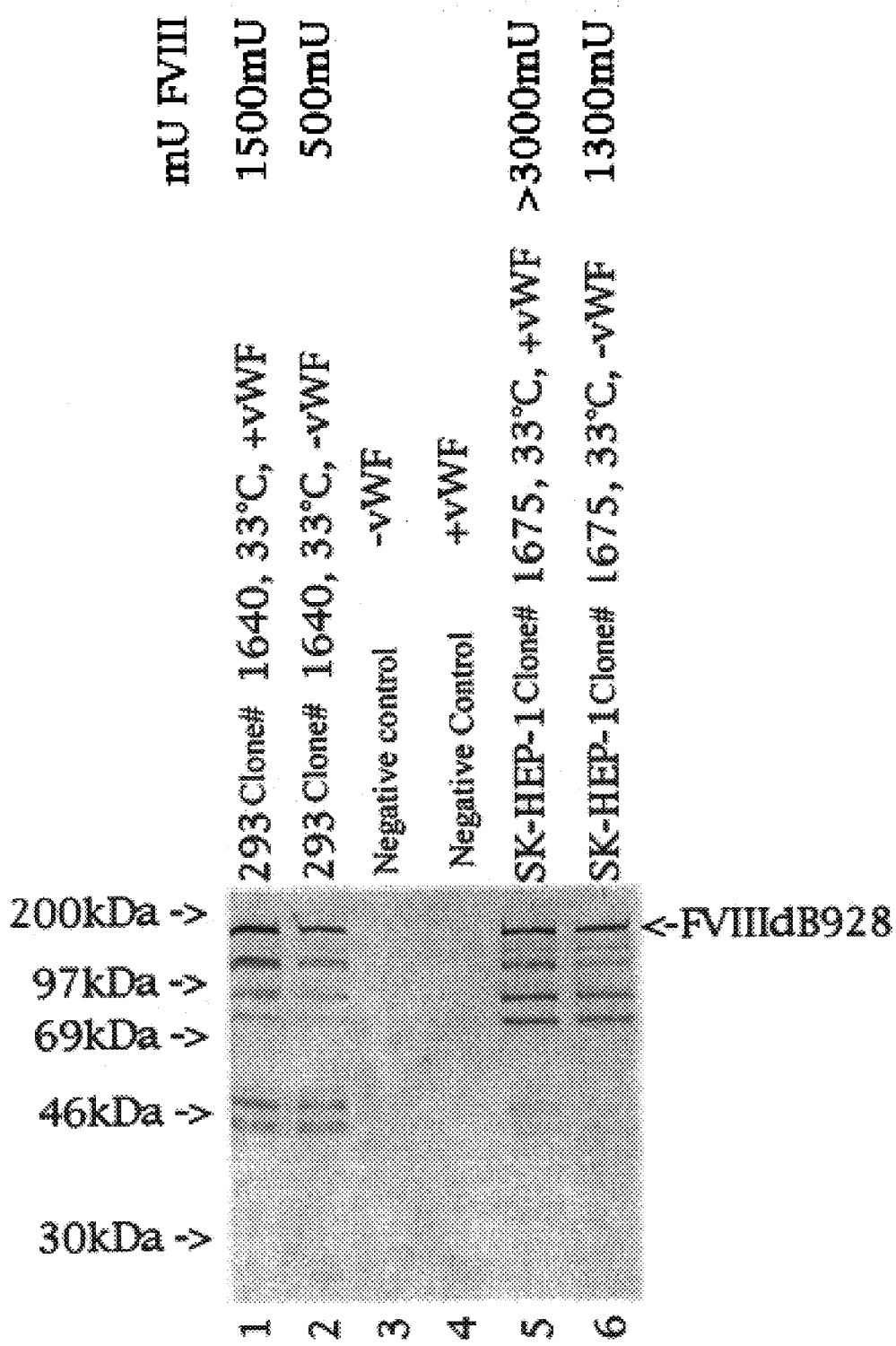
FIG. 9 shows the Western Blot analysis of FVIIIdB928-expressing 293 and SK-HEP-1 cells.

Expression of factor VIII: Expression of FVIIIdB928: The expressed FVIIIdB928 was checked in the Western Blot analysis (FIG. 9). The numbers at the margin indicate the molecular weight in kDa. In addition, the factor VIII activity measured is given in milli-units (mU). It could be shown that the factor VIII specific band spectrum occurred, with the exception of one band at approximately 140 kDa. The factor FVIIIdB928 expressed both, by 293 and by SK-HEP-1 cells has the typical bands which occur in the course of activation of factor VIII. FVIIIdB928, expressed by 293 cells (lanes 1 and 2) differed from factor VIII from SK-HEP-1 cells (lanes 5 and 6) insofar as the bands to a larger extent could be proven at 50, 45 and 43 kDa.

The expression of FVIIIdB928 and of complete factor VIII in 293 and SK-HEP-1 cells is summarized in Table 2.

293 cells initially expressed 100–200 mU FVIIIdB928/10⁶ cells and 24 h; these values could be further increased after sub-cloning.

TABLE 2

|  | 293 cells/ EDH system mU/10⁶ cells | SK-HEP-1 cells(EDH-system mU/10⁶ cells | CHO cells (Dorner et al. JCB 105; 2666 (1987); Kaufman et al., 1988) mU/ml |
|---|---|---|---|
| Initial Selection | FVIIIdB928: 100–200 FVIIIc: 5–10 | FVIIIdB928: 300–1000 FVIIIc: 5–10 | FVIIIdB: not shown FVIIIc: 0.1 |
| Amplification 1500 µg HyB | / | / | / |
| 1 µM MTX | / | FVIIIdB928: 1000–3000 / | / FVIIIdB: 1000–2000 |
| 1 mM MTX +vWF |  |  | FVIIIc: 1000 |

The FVIIIdB928 transfected SK-HEP-1 cells exhibited an initial expression of 300 mU FVIIIdB928/10⁶ cells and 24 h, after sub-cloning this value rose to 500–1000 mU FVIIIdB928/10⁶ cells and 24 h. Starting from 200 µg HyB and rising up to 1500 µg HyB, the amplification led to an expression increase of up to 3000 mU FVIIIdB928/10⁶ cells and 24 h. The amplification via the DHFR portion of the EDH marker was as described in Example 1, since the cell clones illustrated here still had the potential of the expression increase associated with the common DHFR amplification.

Expression of complete factor VIII: The FVIIIc-transfected 293 and SK-HEP-1 cells under HyB selection had a maximum expression of 10 mU FVIIIc/10⁶ cells and 24 h. The further amplification was as described above.

The expression values obtained with the system described herein above all must be judged in the context of the expression data attained in the literature. The FVIIIc/SK-HEP-1 cells described here expressed already initially 10 mU FVIIIc/10⁶ cells and 24 h. A comparison of the expressions of known, B-domain-deleted factor VIII constructs described in the literature with the system described herein yields similar results. In the above-described system of the expression of FVIIIdB928/EDHPro in SK-HEP-1 cells, 1 U FVIIIdB928/10⁶ cells and 24 h could be detected already without MTX amplification. Above all, this value is to be judged taking into consideration the DHFR amplification potential not yet used, which could be utilized for an expression increase of up to 10,000 times, as described in Kaufman et al., 1988, supra. In addition, according to Kaufman et al., 1988, the possibility of the vWF-coexpression enables a further increase of the factor VIII yield.

In summary, the expression of factor VIII in CHO can be compared with that in human liver cells, such as SK-HEP-1 cells, as in Table 3.

TABLE 3

| CHO cells as FVIII expression system | SK-HEP-1 cells as FVIII expression system |
|---|---|
| after initial selection non-detectable expression of B-domain-deleted FVIII and FVIIIc "blind" amplification | high FVIIIdB928 and FVIIIc expression after initial selection thereby specific amplification of those |

TABLE 3-continued

| CHO cells as FVIII expression system | SK-HEP-1 cells as FVIII expression system |
|---|---|
| necessary thereby very high screening expenditure due to the slight FVIII expression a very high amplification is necessary, requiring much time the high amplification requires more screening CHO cells have double minute chromosomes which are associated with un-stable foreign protein expression high amplification causes more genetically and ex-pression-related in-stability differences in the post-translational modification of foreign proteins (e.g. glycosylations) as compared to human proteins possible differences of the FVIII because it was expressed in ovary cells | cell clones which initial-ly express the largest amount of FVIII substantially lower screening expenditure connected therewith saving of time, due to the more rapid production of highly FVIII expressing cell lines due to initially relative high expression of FVIII, lower amplification is sufficient thereby the extent of screening is reduced a lower number of gene copies can be stabilized more easily no species-dependent changes of the post-trans-lational modifications, such as, e.g. glyco-, sylations authentic FVIII, since it was expressed in a liver cell line |

EXAMPLE 3

Expression of von Willebrand factor in transformed cells under particular consideration of human liver cell lines.

Von Willebrand factor (vWF) plays an important role in the platelet adhesion as well as factor VIII-stabilisation. For this reason, coexpression of vWF together with factor VIII was of interest, on the one hand, while also the expression of vWF alone was important, on the other hand.

Figure 11:
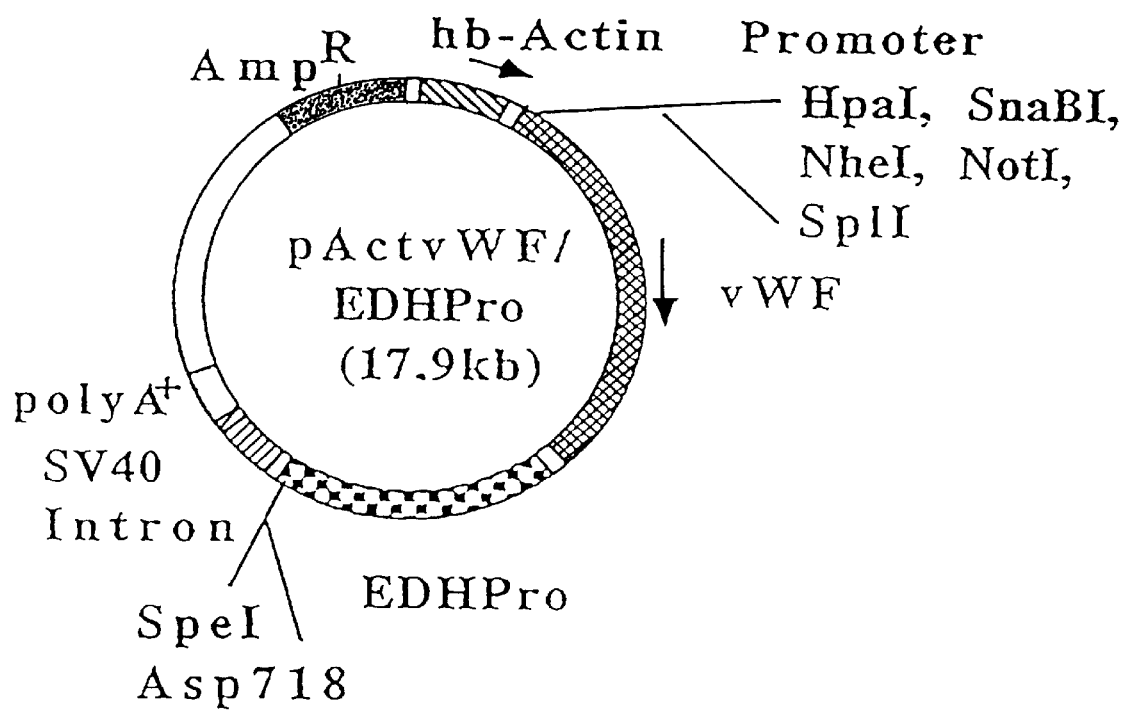
FIG. 11 shows the structure of the plasmid pActvWF/EDHPr.

Construction of the plasmids:

pAct/MCS: pActin comprises the 3.3 kb promoter of the human β-actin gene, as well as 1 kb of the 5' UTR of the β-actin gene. The 5' UTR contains the first intron of the β-actin gene. There follows an MCS, followed by the SV40 polyadenylation site. pActin is based on plasmid pSVβ (MacGregor and Caskey, supra, cf. Example 1). From the resulting plasmid pSVMCS, the EcoRI-SalI fragment containing the SV40 promotor/enhancer and the SV40 16/19S intron was removed; instead, the EcoRI-SalI fragment from pHβAPr-1 containing the actin promotor and the 5' UTR actin intron (Gunning et al., PNAS 84: 4831, 1987) was inserted. This plasmid was named pActin. This plasmid was cleaved with ClaI and SalI and ligated with the oligonucleotides #1293, 5' TCG ATG TTA ACT ACG TAG CTA GCG CGG CCG CCG TAC GTC GCG AGT CGA CAA TAT TGA TAT CGG TAC CGG TAC CAC TAG TGT 3' (SEQ.ID.No. 22) and #1294, 5' CGA CAC TAG TGG TAC CGG TAC CGA TAT CAA TAT TGT CGA CTC GCG ACG TAC GGC GGC CGC GCT AGC TAC GTA GTT AAC A 3' (SEQ.ID.No.23). From this, construct pAct/MCS formed.

pAct/EDHPro: pAct/MCS was cleaved with EcoRV, and the 2200 bp EDHPro fragment was inserted as SmaI and BglII, Pol.K. treated fragment from pCMV/EDHPro, so that the plasmid pAct/EDHPro was formed.

pActvWF/EDHPro: An EcoRI fragment cleaved from ph-Act-vWF (Fischer et al., FEBS Letters 351; 345 (1994) containing the complete cDNA of the human vWF as well as approximately 200 bp 5' and 130 bp 3' UTR is filled in with Pol. K. and inserted into the NruI cleavage site of pAct/EDHPro. From this, plasmid pActvWF/EDHPro resulted (FIG. 11).

Apart from the complete coding region of the vWF, this fragment contains 200 bp of the untraslated (UTR) 5' region and 150bp of the untranslated 3' region.

Production of the permanent cell lines: Initial selection and amplification were effected as described in Example 2.

vWF quantitation by means of ELISA: vWF quantitation was effected by means of the ELISA system obtainable from Boehringer Mannheim, Federal Republic of Germany ("Asserachrom vWF, No. 136 0272).

Protein detection by means of Western Blot analyses: The Western Blot analyses were carried out as described in Example 2. As the first antibody, a polyclonal rabbit-anti-vWF antibody (Dakopatts, Denmark) was used in a dilution of 1:100. As the second antibody, a goat-anti-rabbit antibody (BioRad, CA, USA) was used in a dilution of 1:7500.

Examination of the DNA and RNA structures: The preparations of DNA and RNA were effected as described in Example 1. For hybridizing within the context of Southern Blot analyses or Northern Blot analyses, respectively, vWF, dhfr and hph fragments were isolated from the respective plasmids (also from pActvWF/EDHPro, pSVDHFR, pCMV/Hy).

Production and analysis of pActvWF/EDHPro transfected cell lines: Analogous to the descriptions of Example 2, 293 and SK-HEP-1 cells were transfected with the expression plasmid pActvWF/EDHPro, and cell lines stably-expressing vWF were selected and characterized by Southern Blot analyses. Following upon the selection with HyB, both 293 and SK-HEP-1 cells were amplified via the dhfr unit of the EDH marker, starting from 100 nM MTX. In both cases, vWF was expressed in large amounts. The identity of the expressed vWF with plasmatic vWF was determined by means of Western Blot analyses. vWF quantitation was effected by means of ELISA determinations. In addition, the ristocetin-induced thrombocyte aggregation was examined by means of the corresponding test of Behringwerke (OUBD, von Willebrand reagent).

EXAMPLE 4

Expression of recombinant human factor IX in SK-HEP-1 and 293 cells.

From a randomly primed human liver lambda gt10 phage library, the cDNA of human factor IX was isolated. The factor IX cDNA fragment comprises 4 nucleotides of the 5' UTR and 48 nucleotides of the 3' UTR in addition to the encoding region. This 1.4 kb fragment, flanked by EcoRI linkers subsequently was inserted into the EcORI site of plasmid Bluescript II KS- (Strategene). This plasmid was named pBlueII KS-FIX.

Figure 12:
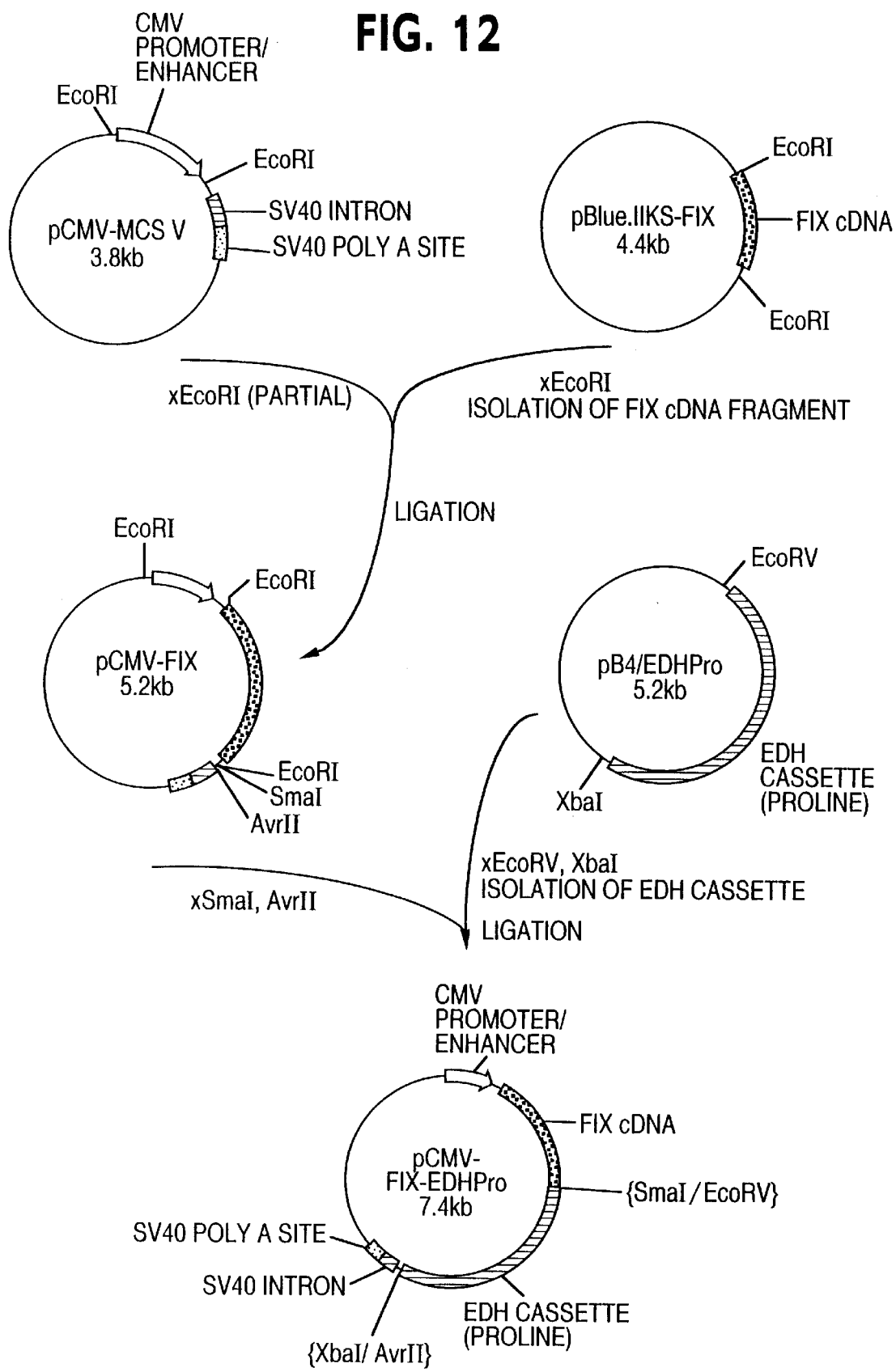
FIG. 12 shows the construction of PCMV-FIX-EDHPro.

As schematically described in FIG. 12, by means of standard cloning methods (Maniatis et al., supra), the factor IX cDNA is inserted as the EcoRI fragment into plasmid pCMV-MCS V which is also EcoRI cleaved and results in pCMV-FIX. pCMV-MCS-V is a plasmid derived from pCMV-MCS (cf. Example 1); into its XhoI site, the MCS with the sequence 5'-TCGAATCGA TTGAATTCCC CGGGGTCCTC TAGAGTCGAC CTGCAGAAGC TTAGTACTAG TAGGCCTAGG GCCCTATCGA-3' (SEQ.ID.No. 24) was inserted.

The resulting plasmid pCMV-FIX was opened with SmaI and AvrII, and the EDH cassette from plasmid pB4/EDHPro was inserted as EcoRV/XbaI fragment. The resulting plasmid is pCMV-FIX-EDHPro.

pB4/EDHPro: The EDH cassette was isolated from pCMV/EDHPro as SmaI, BglIII fragment and inserted into the Sma-,BamHI-cleaved vector pBluescript II SK- (Pharmacia, Sweden). 293 (ATCC, CRL 1573) and SK-HEP-1 (ATCC, HTB 52) cells; growing routinely in DMEM/Ham's F12 medium, supplemented with 2 mM glutamine and 10% fetal calf serum, were made to take up pCMV-FIX-EDHPro by means of the $CaPO_4$ method or by electroporation (BioRad Gene Pulser). Two days after DNA uptake, the cells were plated in various cell densities, and the medium was supplied with 100 µg (293) or 200 µg (SK-HEP-1) of hygromycin B/ml for selection. Two weeks later, the resulting cell clones were isolated and grown to confluency. In serum-free 24 hour cell culture supernatants supplemented with 10 µg of vitamin $K_1$/ml, subsequently the amount of antigen (ELISA), functionality (corresponding activity tests) and qualitative integrity (Western Blot analysis) of the secreted, recombinant protein were examined. The cell number was determined after trypsinizing the cells (in the cell number measuring apparatus of Schärfe, Reutlingen, Germany).

For factor IX antigen determination, the test kit of Boehringer Mannheim (Asserachrom Factor FIX-Ag, Diagnostica Stago) was used, wherein a reference plasma (the IMMUNO reference plasma 5220005) was used for providing the standard curve.

To detect the coagulation activity, a one-step coagulation test was utilized by using an Amelung KC10 Coagulometer. Therein, at first equal portions of the sample to be determined, of factor IX deficiency plasma and of phospholipid/kaolin activator solution were each incubated at 37° C. for 4 min, whereupon one portion of 25 mmol $CaCl_2$ was added to start the reaction, the coagulation time was measured, and determined with a standard curve made by means of a factor IX standard.

For the Western Blot analysis, 10 µl of cell culture supernatant were reduced and denatured, and separated in denaturing 4% stacking/8% separating gels according to L ämmli (Nature 227: 680, 1970) by means of the BioRad Mini-Protean II Dual Slab Gel System (BioRad Laboratories, Richmond, Calif., USA). Afterwards, the proteins were transferred in transfer buffer (25 mM Tris, 192 mM glycine) to nitrocellulose membranes with the BioRad Mini Trans-Blot-System (BioRad Laboratories, Richmond, Calif., USA). To visualize the recombinant protein, the Protoblot System of Promega (Madison, Wis., USA) was used. Rabbit-anti-factor IX serum of Dakopatts (Glostrup, Denmark) was used as antibody for factor IX binding. The activity and antigen yields of typical cell clones and associated negative controls are listed in Table 4.

TABLE 4

Expression of recombinant factor IX in 293 and SK-HEP-1 cell clones

| Sup-No. | hr-Protein | µg/ml (Antigen) | mU/ml (Activity) | Cell line | Activity/ Antigen |
|---|---|---|---|---|---|
| 520-72 | Factor IX | 1.4 | 127 | 293 | 0.36 |
| 520-168 | Factor IX | 2.2 | 96 | 293 | 0.17 |
| 520-240 | Factor IX | 1.0 | 47 | 293 | 0.19 |
| 543-1 | none | 0 | 0 | 293 | Neg. control |
| 550-336 | Factor IX | 1.0 | 298 | SK-HEP-1 | 1.19 |
| 550-360 | Factor IX | 0.9 | 267 | SK-HEP-1 | 1.19 |
| 550-96 | Factor IX | 2.0 | 288 | SK-HEP-1 | 0.58 |
| 551-24 | none | 0 | 0 | SK-HEP-1 | Neg. control |

1 unit factor IX corresponds to 4 µg/ml. Cells grown at 10 µg vitamin $K_1$/ml.
Antigen determined by ELISA, activity by coagulation test.

In principle, it can be concluded from the expression data that, compared to the CHO expression system described in the literature, with the expression system according to the invention considerably higher expression values of recombinant factor IX can be obtained in SK-HEP-1 and 293 cells already with non-amplified initial cell clones, and the portion of functional factor IX of total factor IX is substantially higher. A further advantage of the selection system described here is represented by the fact that, of all the clones isolated after transfection/electroporation, practically all (>95%) produce recombinant factor IX; this is very much in contrast to the usual CHO dhfr expression system, in which only a fraction of the isolated clones produce factor IX, both, in case of cotransfection and when using bicistronic mRNAs without internal ribosome binding sites (Ehrlich et al., JBC 264: 14298, 1989).

Figure 13:
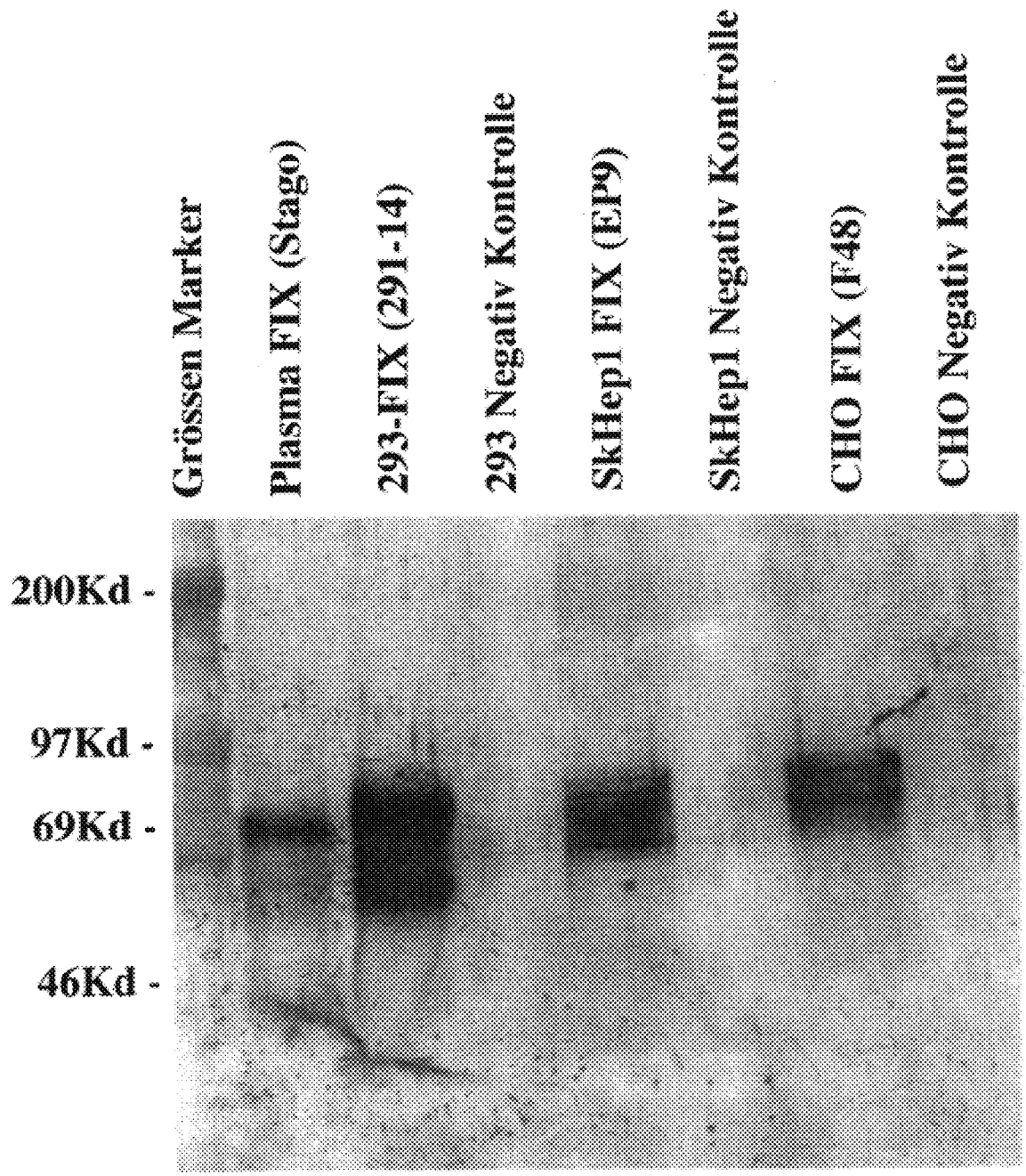
FIG. 13 shows a Western Blot of recombinant factor IX from 293 and SK-HEP-1 cell clones as compared to plasmatic factor IX and recombinant factor IX from CHO cells.

FIG. 13 shows the Western Blot of recombinant factor IX from representative 293 and SK-HEP-1 cell clones as compared to plasmatic factor IX and recombinant factor IX from CHO cells.

Recombinant factor IX from all three cell lines exhibits a molecular weight comparable to that of plasmatic factor IX. 293 factor IX was obtained from 293 clone 291-14, SK-HEP-1 factor IX was obtained from cell clone EP 9. As a control, also recombinant factor IX from the CHO cell clone F 48 provided by means of conventional factor IX/dhfr cotransfection, was applied. 293, SK-HEP-1 and CHO cells which do not contain expression plasmids do not produce factor IX.

With the expression data, it should be particularly pointed out that the amplification potential has not yet been utilized in the present example. After amplification has been accomplished, the yields can be increased dramatically.

EXAMPLE 5

Expression of recombinant human protein C in SK-HEP-1 and 293 cells

From a randomly primed human liver cell λgt10 phage library, the cDNA of human protein C was isolated. In addition to the encoding region, the cDNA also contains 100 bp of the untranslated (UTR) 5' region and 500 bp of the untranslated 3' region and is flanked on both sides by EcoRI cleavage sites. This 1.9 kb fragment was inserted into the EcoRI site of plasmid pUC13 (Pharmacia) and named pPrtC-1.

Compared to the published protein C sequence (Beckman et al., NAR 13:5233, 1985; Foster and Davie, PNAS 81:4766, 1984), pPrtC-1 contains two differences on amino acid level: Codon 76 of the mature protein C contains the triplet CTC instead of the published sequence TTC (this results in an amino acid exchange from PHE to LEU); on the other hand, pPrtC-1 has an in-frame deletion of those 5 codons (5'-GGC GAC AGT GGG GGG-3') (SEQ ID No.29) encoding the amino acids 358 to 362 (GLY-ASP-SER-GLY-GLY) (SEQ ID No:30) of mature protein C.

By means of standard cloning methods, a 1.5 kb protein C fragment (which contains the 5' UTR, yet merely 15 bp of the 3' UTR) was cleaved from pPrtC-1 with PstI and inserted into the pTM3 opened by PstI (Moss et al., Nature 348:91, 1990); the resulting plasmid is pTM3-PrtC.

By using a mutagenesis kit (Sculptor In Vitro Mutagenesis Kits (Amersham)) and the DNA primer 5'-TGTGAGCTGCCCCATGGTGGAGGCACTGGC 3' (SEQ.ID.No. 25), the DNA sequence in pTM3-PrtC overlapping with the translation initiation codon ATG was converted into a NcoI cleavage site. The resulting plasmid was NcoI-cleaved and religated to fuse the NcoI cleavage site located in pTM3 to the newly created NcoI cleavage site at the 5' end of the encoding region of the PrtC-cDNA. Thus, the entire 5' UTR of ProtC-cDNA was successfully deleted.

By aid of the Sculptor In Vitro Mutagenesis Kit and the primer 5'-GTGGAAGGAGGCGACCATGGGCCCCCCACTGT-CGCCCTCGCAGGCATCCTGCCGG TC-3' (SEQ.ID.No. 26), at first the missing 15 nucleotides were re-inserted into pTM3-PrtC sodas to repair the above-mentioned deletion. The resulting plasmid was named pTM3-PrtCpt. mut. (FIG. 14).

In an analogous manner, the point mutation in codon 76 in pTM3-PrtCpt. mut. finally was changed with the primer 5'-GCAGTCGCAGCTGAAGCTGCCGAT-3' (SEQ.ID.No. 27) into the wild type sequence. The resulting plasmid was named pTM3-PrtCwt.

Figure 14:
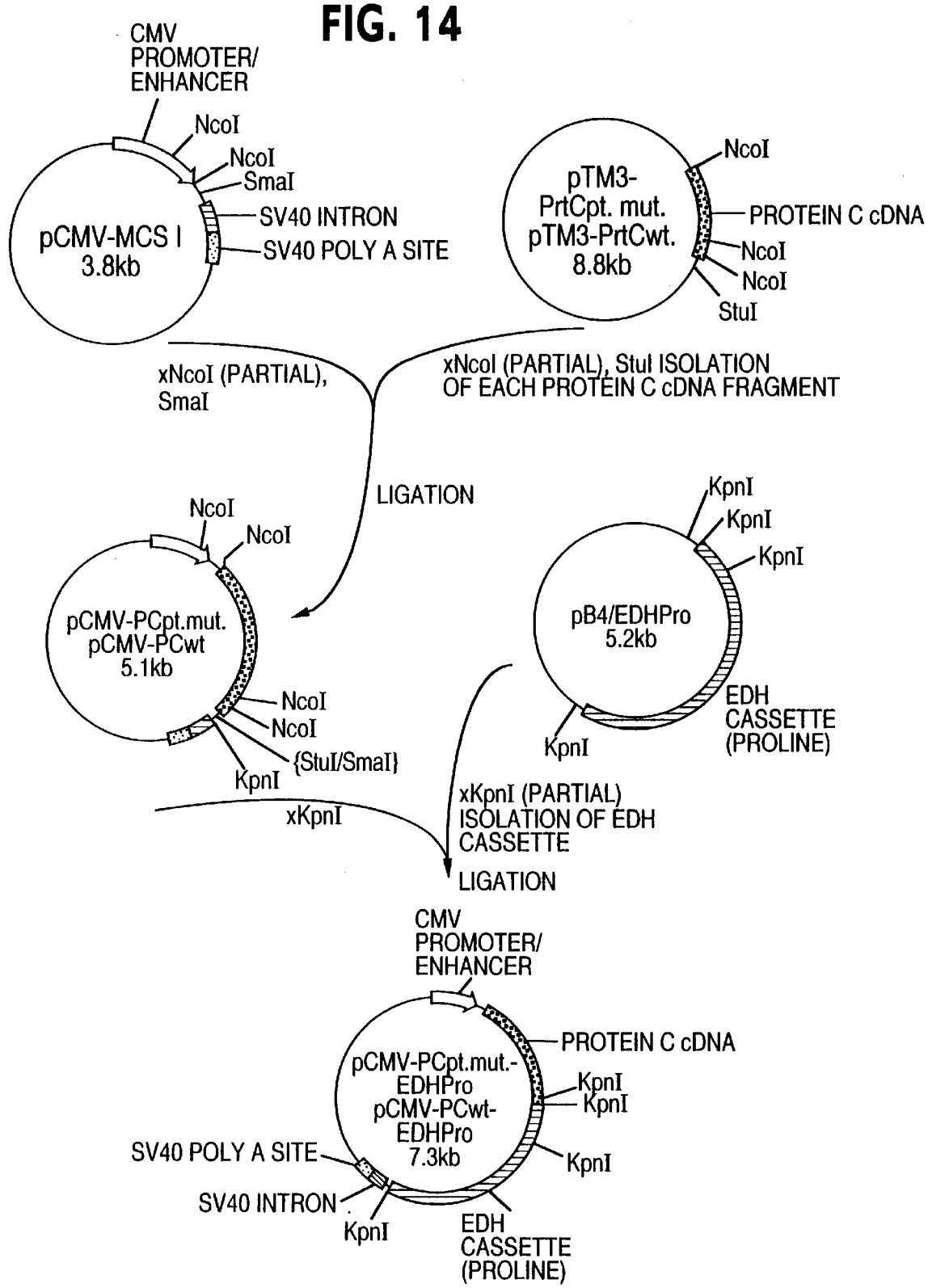
FIG. 14 shows the construction of pCMV-PCwt-EDHPro and PCMV-PCpt.mut.-EDHPro.

As schematically described in FIG. 14, the PCwt or PCpt. mut. cDNA fragments, respectively, from pTM3-PCwt. or pTM3-PCpt. mut., respectively, were put into the NcoI, SmaI-cleaved plasmid pCMV-MCS I as NcoI-, StuI-fragment. PCMV-MCS I is a descendant of the plasmid pCMV-MCS. This plasmid contains the immediate early gene promotor/enhancer of human cytomegalovirus and 80 bp of the 5' UTR of the associated gene. There follows the MCS with the sequence 5'-TCGACCATGGAAGCTTATCGATCCCGGGAA TTCGGTACCG TCGACCTTGCA GGTGCACGGG CCCAGATCTG ACTGATCGA-3' (SEQ.ID.No. 28), followed by the SV40 16 S/19 S intron and the SV40 poly-adenylating site.

The resulting plasmids pCMV-PCwt and pCMV-PCpt. mut., respectively, were opened with KpnI, and the EDH cassette from plasmid pB4/EDHPro (cf. Example 4) was inserted as KpnI fragment. The resulting plasmids are pCMV-PCwt-EDHPro and pCMV-PCpt.mut.-EDHPro, respectively.

Both plasmids were introduced in 293 (ATCC, CRL 1573) and SK-HEP-1 (ATCC,HTB 52) cells, as described in Example 4, and cell clones were isolated.

In the serum-free 24 hour cell culture supernatants supplemented with 10 µg vitamin $K_1$/ml, subsequently the antigen amount (ELISA), the functionality (appropriate activity test), and the qualitative integrity (Western Blot analysis) of the secreted, recombinant protein were examined. The cell number was determined after trypsinizing the cells (in the cell number measuring apparatus of Schärfe, Reutlingen, Germany).

For the protein C-antigen determination, a test kit (Asserachrom Factor Protein C-Ag, Diagnostica Stago, of Boehringer Mannheim) was used, wherein a co-supplied standard was used for providing the standard curves.

To detect the coagulation activity, a one-step coagulation test was utilized, by using an Amelung KC4 coagulometer. Equal portions of the sample to be determined, protein C deficient plasma, Protac and phospholipid/kaolin activator solution were incubated at 37° C. for 4 min, subsequently one portion of 25 mmol $CaCl_2$ was added to start the reaction, the coagulation time was measured, and determined by means of a standard curve provided by a protein C standard.

For carrying out the Western Blot analysis, 10 µl cell culture supernatant were reduced and denatured, and separated in denaturing 4% stacking/10% separating gels according to Lämmli (Nature 227: 680, 1970) by the BioRad Mini-Protean II Dual Slab Gel system (BioRad Laboratories, Richmond, Calif., USA). After the gel run, the proteins were transferred by the BioRad Mini Trans-Blot-System (BioRad Laboratories, Richmond, Calif., USA) in transfer buffer (25 mM Tris, 192 mM glycine) to nitrocellulose membranes. To visualize the recombinant proteins, the Protoblot-System of Promega (Madison, Wis., USA) was used. Rabbit-anti-protein C serum (Dakopatts; Glostrup, Denmark) was used as the antibody for binding protein C.

Figure 15:
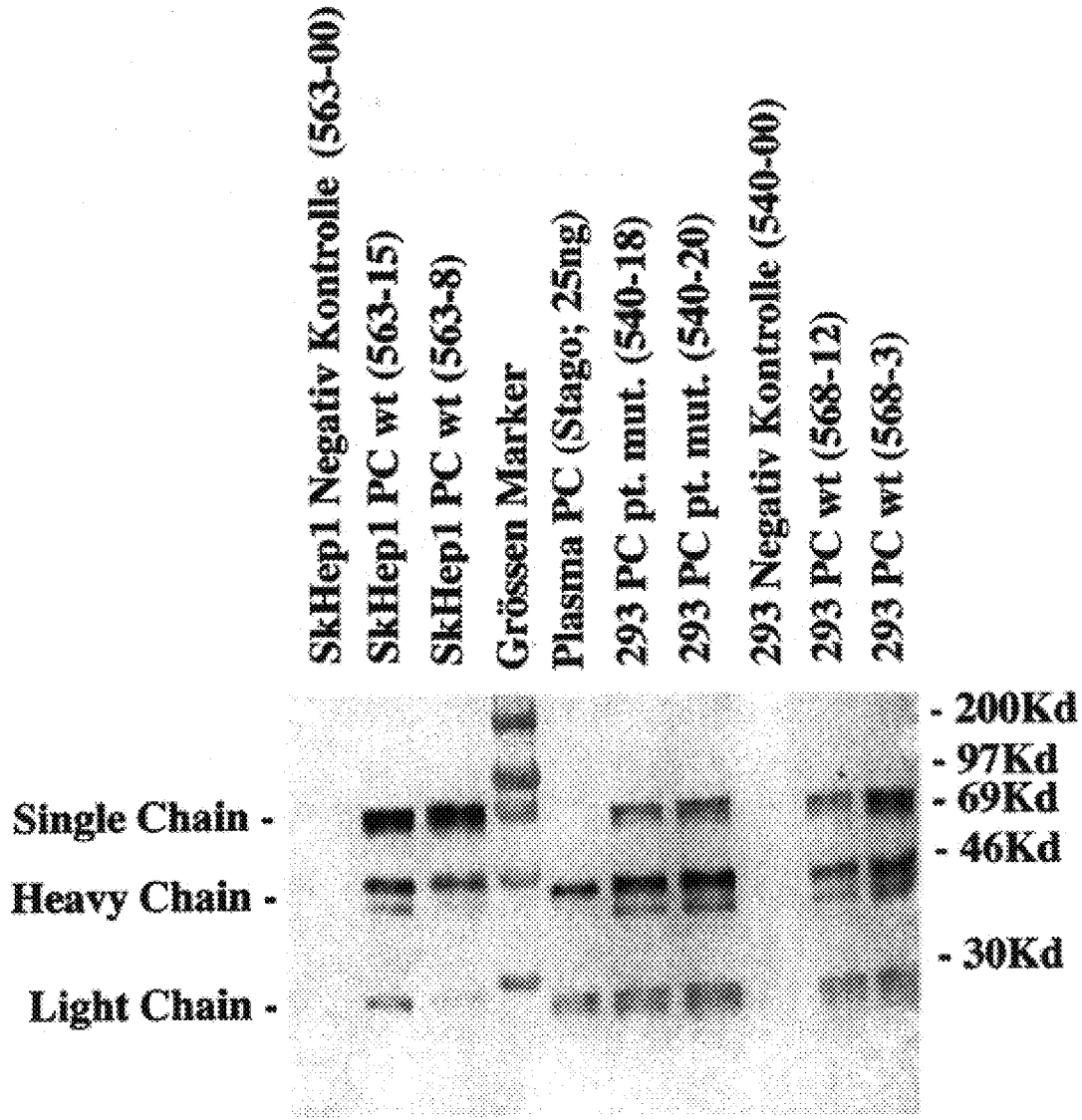
FIG. 15 shows a Western Blot of recombinant protein C from 293 and SK-HEP-1 cells as compared to plasmatic protein C.

Activity and antigen yields of typical cell clones and associated negative controls are listed in Table 5. FIG. 15 shows the Western Blot of recombinant protein C from 293 and SK-HEP-1 cells as compared to plasmatic protein C.

While no protein C can be detected in non-transfected SK-HEP-1 (sample 563-00) and 293 (540-00) cells, 293 and SK-HEP-1 cells transfected with either wt or point-mutated protein C cDNA do exhibit a corresponding expression. In all the cases, heavy and light chains of the protein C are detectable, similar to the plasmatic protein C. However, merely 50% (clones 568-12, 568-3) and 30% (clones 563-15, 563-8) of the wt protein C produced by 293 and SK-HEP-1, respectively, cells are processed into heavy and light chains, while the remaining material is present as un-processed single-chain molecule. In contrast thereto, the major portion of the point-mutated protein C is processed into heavy and light chains, as can be seen in the supernatants of the two 293 cell clones 540-18 and 540-20. The molecular weights of a co-applied size marker are indicated at the right-hand side of FIG. 15.

The article by Grinnell et al., Adv. Appl. Biotechnol. Series 11: 29–63, 1990, summarizes the wt protein C expression data of the working group at Eli Lilly. From this it is apparent that with initial-selected, non-amplified cell clones the maximum expression data reached did not exceed 1.15 $\mu g/10^6$ cells and day; in contrast thereto, with the expression system described by us, however, expression rates higher by three times are very much possible, as has been demonstrated for clone 568-12 (Table 5).

Figure 16:
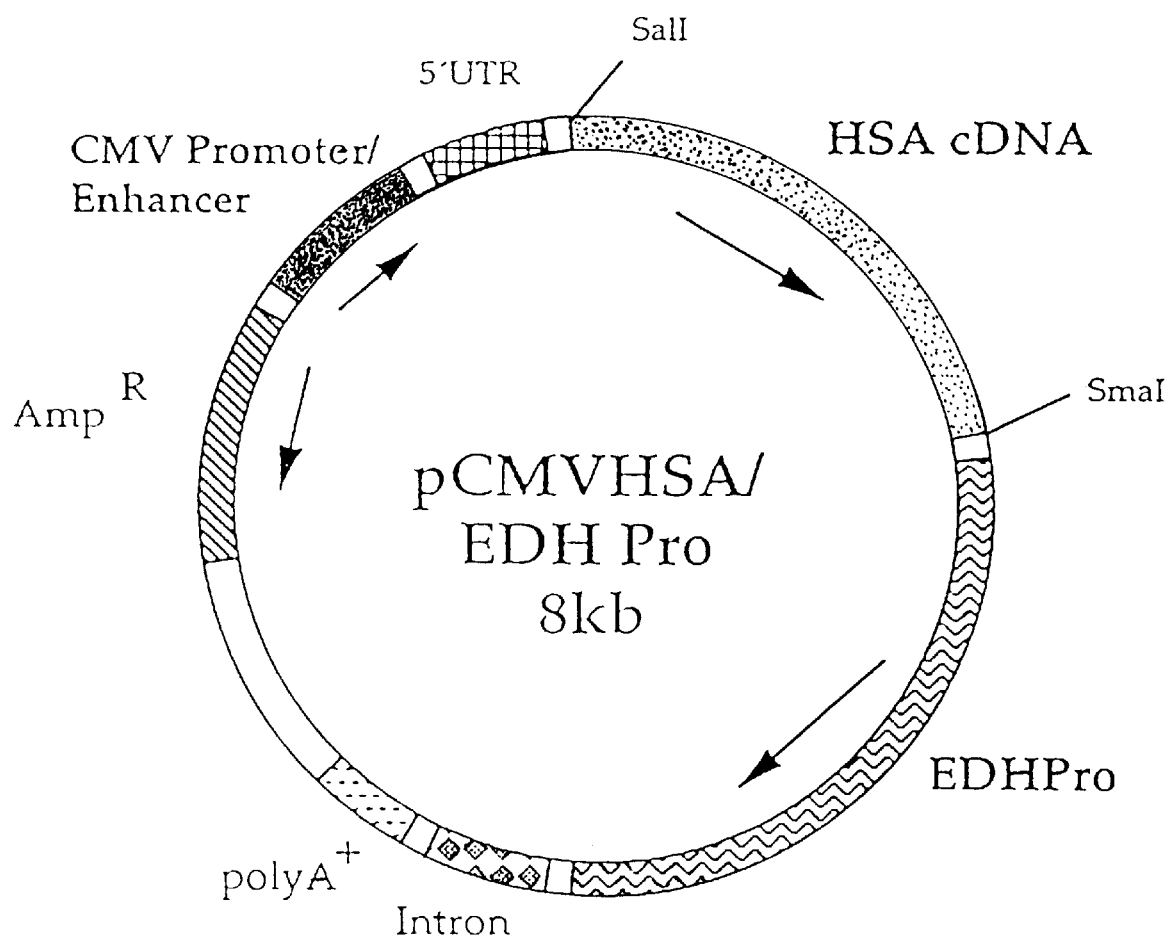
FIG. 16 shows the schematic illustration of the plasmid pCMVHSA/EDHPro.

Construction of the HSA expression plasmid:

The expression plasmid pCMVFVIIIdB928/EDHPro (cf. Example 2) was cleaved with SmaI and SalI, the FVIII-cDNA was removed and ligated with the SmaI, SalI-cleaved HSA-cDNA from pAlb4. This led to expression plasmid pCMVHSA/EDHPro (FIG. 16).

Figure 17:
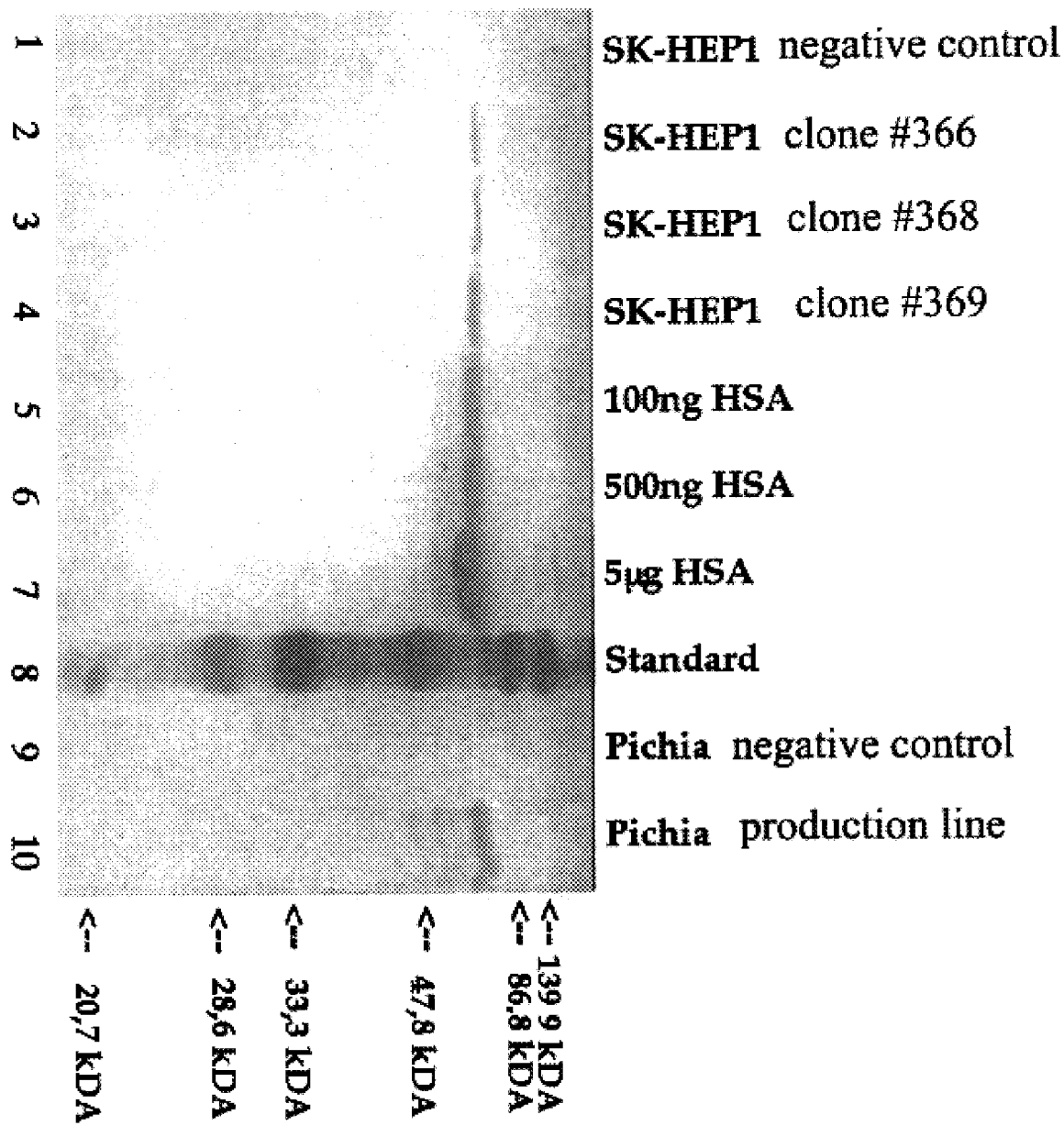
FIG. 17 shows a Western Blot analysis of HSA expressing SK-HEP-1 cells. The numbers at the margin indicate the molecular weight in kDa. Lane 1, SK-HEP-1 negative control; lane 2, SK-HEP-1 clone #366; lane 3, SK-HEP-1 clone #368; lane 4, SK-HEP-1 clone #369; lanes 5–7, plasmatic HSA standards; lane 8, molecular weight standard; lane 9, Pichia p. negative control; lane 10, HSA-expressing Pichia p. production strain.

Production and analysis of pCMVHSA/EDHPro-transfected cell lines:

Analogous to the descriptions of Example 2; SK-HEP-1 cells were transfected with the expression plasmid pCMVHSA/EDHPro and stably HSA-expressing cell lines were selected. The selection was carried out with HyB, starting at 200 $\mu g/ml$ and subsequently was increased to 400 $\mu g/ml$. Following the selection with HyB, the SK-HEP-1 cells were amplified via the dhfr unit of the EDH marker, starting with 100 nM MTX. At the stage of 400 $\mu g$ HyB, up to 1.7 $\mu g$ HSA/$10^6$ cells and 24 hours and 2.6 $\mu g$ HSA/ml could be detected. The identity of the expressed HSA was determined by comparison with plasmatic HSA and with HSA from Pichia pastoris was determined by means of Western Blot analysis (FIG. 17). HSA quantitation was effected by means of ELISA determinations.

Materials and methods

Construction of the plasmids:

pCMVHSA/EDHPro: pCMVFVIIIdB928/EDHPro was cleaved with SmaI and SalI, and the FVIIIdB928 fragment was substituted by the SmaI, SalI-cleaved HSA fragment from pAlb4 (FIG. 17). pAlb4 is composed of pBluescript 4 SK and HSA cDNA (Lawn et al., Nucleic Acid Res. 9: 6103–6114, (1981); Dugaiczyk et al., PNAS 79: 71–75 (1982)).

Production of the permanent cell lines:

Initial selection and amplification were as described in Example 2.

HSA quantitation by means of ELISA:

The HSA quantitation in ELISA was effected by means of the monoclonal anti-HSA-antibody (Pierce) and by means of the rabbit-anti-HSA-antibody serum obtainable from Dakopatts, Denmark, which was present directly coupled with peroxidase.

Protein detection by means of Western Blot analyses:

The Western Blot analyses were carried out according to the descriptions given in Example 2. As the first antibody, a monoclonal Anti-HSA-antibody (Monosan; Sanbio, The

TABLE 5

Expression of rProtein C wt and pt. mut. in 293 and SK-HEP-1 Cell Cones

| Sup-No. | hr-Protein | $\mu g/ml$ (Antigen) | mU/ml (Activity coag. inh.) | mU/ml (Activity amid. test) | $\mu g/10^6$ Cells | Cell line | Activity/Antigen (coag. inh.) |
|---|---|---|---|---|---|---|---|
| 563-15 | PC wt | 4.7 | 130 | 130 | 1.8 | SK-HEP-1 | 0.11 |
| 563-8 | PC wt | 2.5 | n.c. | 75 | 1.3 | SK-HEP-1 | n.c. |
| 540-18 | PC pt. mut. | 1.4 | 185 | 112 | 0.38 | SK-HEP-1 | 0.53 |
| 540-20 | PC pt. mut. | 1.2 | 193 | 103 | 0.41 | SK-HEP-1 | 0.64 |
| 563-00 | none | 0 | 0 | 10 | — | SK-HEP-1 | Neg. control |
| 540-00 | none | 0 | 0 | 0 | — | 293 | Neg. control |
| 568-12 | PC wt | 11.4 | >1000 | 470 | 3.2 | 293 | >0.35 |
| 568-3 | PC wt | 3.4 | 645 | 178 | 1.1 | 293 | 0.76 |

1 unit protein C corresponds to 4 $\mu g/ml$. Cells grown at 10 $\mu g$ vitamin $K_1/ml$.
Antigen determined by ELISA, activity by amidolytic test and coagulation inhibition test.
'n.c' means 'not carried out'.

EXAMPLE 6
Expression of human serum albumin (HSA) in transformed SK-HEP-1 cells

Netherlands) in a dilution of 1:500 was used. As the second antibody, a goat-anti-mouse-antibody (BioRad, USA) in a dilution of 1:7500 was used.

What is claimed is:

1. A method for producing a protein comprising:
   (a) transfecting an eukaryotic cell line expressing an endogenous dihydrofolate reductase (dhfr) gene with an expression plasmid to obtain clones, wherein said expression plasmid comprises a dicistronic transcription/translation unit comprising:
      (i) a sequence encoding said protein; and
      (ii) a sequence encoding a fusion protein comprising the coding sequence of a dominant selection marker gene and a dihydrofolate reductase (dhfr) gene that expresses a wild-type dhfr phenotype as an amplification marker, wherein said sequence encoding said fusion protein is located 3' to said sequence encoding said protein, and wherein said dicistronic transcription/translation unit further comprises an internal ribosome binding site between the sequence encoding the protein and the sequence encoding the fusion protein,
   (b) isolating said clones obtained by said transfection step controlled by said selection marker,
   (c) amplifying said selected clones in a first amplification,
   (d) subsequently further amplifying said clones in a further amplification controlled by said amplification marker, thereby expressing said protein, and
   (e) obtaining said expressed protein.

2. A method as set forth in claim 1, wherein said first amplification occurs while selecting said clones obtained.

3. A method as set forth in claim 1, wherein said selection process is effected by using hygromycin B and said further amplification is effected by using methotrexate.

4. A method as set forth in claim 1, wherein said eukaryotic cell line transfected with said expression plasmid is selected from the group consisting of a Chinese Hampster Ovary cell line, a human kidney cell line, and a human liver cell line.

5. A method as set fourth in claim 1, wherein said eukaryotic cell lines transfected with said expression plasmid are selected from the group consisting of CHO, 293 and human liver cell lines, such as SK-HEP-1 and Chang liver.

6. A method as set forth in claim 1, wherein said protein is a recombinant blood coagulation factor or a viral protein.

7. A method as set forth in claim 1, wherein said protein is recombinant human prothrombin, recombinant human factor VIII, recombinant human FVIIIdB928, a recombinant human factor IX, recombinant human protein C, recombinant human von Willebrand factor or recombinant human serum albumin.

8. A method according to claim 1, wherein said internal ribosome binding site is the 5'-untranslated region of the encephalomyocarditis virus (EMCV 5' UTR).

9. A method according to claim 1, wherein said sequence encoding the protein is 5' and said sequence encoding the fusion protein is 3' from said internal ribosome binding site.

10. A method according to claim 1, further comprising a spacer sequence, said spacer sequence separating said dominant selection marker gene and said dihydrofolate reductase (dhfr) gene of said sequence encoding a fusion protein.

11. A method according to claim 1, wherein said dominant selection marker is selected from the group consisting of adenosine deaminase, hygromycin phosphotransferase and neomycin transferase.

12. A method according to claim 1, wherein said sequence encoding a protein comprises a sequence encoding a human plasma protein, a viral protein, a derivative thereof or a fragment thereof.

13. A method according to claim 12, wherein said sequence encoding a protein comprises a sequence encoding human prothrombin cDNA.

14. A method according to claim 12, wherein said sequences encoding a protein comprises a sequence encoding human factor VIII cDNA.

15. A method according to claim 12, wherein said sequences encoding a protein comprise a sequence encoding human factor VIII dB928 cDNA.

16. A method according to claim 12, wherein said sequences encoding a protein comprise a sequence encoding human factor IX cDNA.

17. A method according to claim 12, wherein said sequences encoding a protein comprise a sequence encoding human protein C cDNA.

18. A method according to claim 12, where said sequences encoding a protein comprise a sequence encoding human von Willebrand factor cDNA.

19. A method according to claim 1, wherein the expression plasmid is selected from the group consisting of pCMVFII/EDH-Sp, pCMVFII/EDHGly and pCMVFII/EDHPro.

20. A method according to claim 1, wherein the expression plasmid is selected from the group consisting of pCMVFVIIIc/EDH-Sp, pCMVFVIIIc/EDHGly and pCMVFVIIIc/EDHPro.

21. A method according to claim 1, wherein the expression plasmid is selected from the group consisting of pCMVFVIIIdB928/EDH-Sp, pCMVFVIIIdB928/EDHGly and pCMVFVIIIdB928/EDHPro.

22. A method according to claim 1, wherein the expression plasmid is selected from the group consisting of pCMVFIX/EDH-Sp, pCMVFIX/EDHGly and pCMVFIX/EDHPro.

23. A method according to claim 1, wherein the expression plasmid is selected from the group consisting of pCMV-PCwt-EDH-Sp, pCMV-PCwt-EDHGly, pCMV-PCwt-EDHPro, pMCV-PCpt. mut.-EDH-Sp, pCMV-PCpt.mut.-EDHPro and pCMV-PCpt. mut.-EDHGly.

24. A method according to claim 1, wherein the expression plasmid is selected from the group consisting of pAct-vWF-EDH-Sp, pACT-vWF-EDHPro and pACT-vWF-EDHGly.

25. A method according to claim 1, wherein said expression plasmid comprises at least one expression cassette containing DNA sequences selected from the group consisting of SEQ.ID.No. 6, SEQ.ID.No. 7 and SEQ.ID.No. 8.

26. A method as set forth in claim 5, wherein said eukaryotic cell line is 293 or SK-HEP-1.

27. A method for producing a protein comprising:
(a) transfecting SK-HEP-1 cells with an expression plasmid to obtain clones, wherein said expression plasmid comprises a dicistronic transcription/translation unit comprising:
(i) a sequence encoding said protein, and
(ii) a sequence encoding a fusion protein comprising the coding sequence of a dominant selection marker gene and a dihydrofolate reductase (dhfr) gene that expresses a wild-type dhfr phenotype as an amplification marker, wherein said sequence encoding said fusion protein is located 3' to said sequence encoding said protein, and wherein said dicistronic transcription/ translation unit further comprises an internal ribosome binding site between the sequence encoding the protein and the sequence encoding the fusion protein,
(b) isolating said clones expressing said protein, and
(c) obtaining said expressed protein.

28. A method according to claim 27, wherein said protein is selected from the group consisting of prothrombin, factor VIII, factor VIII deletion mutant, factor IX, protein C, von Willebrand factor and serum albumin.

29. A method for producing a protein comprising:
(a) transfecting SK-HEP-1 cells with an expression plasmid comprising the coding sequence of a blood factor protein selected from the group consisting of prothrombin, factor VIII, factor VIII dB928, a factor VIII deletion mutant, Factor IX, protein C, von Willebrand factor, serum albumin, a derivative thereof and fragment thereof to obtain clones, wherein said expression plasmid comprises a dicistronic transcription/translation unit comprising:
(i) a sequence encoding said protein, and
(ii) a sequence encoding a fusion protein comprising the coding sequence of a dominant selection marker gene and a dihydrofolate reductase (dhfr) gene that expresses a wild-type dhfr phenotype as an amplification marker, wherein said sequence encoding said fusion protein is located 3' to said sequence encoding said protein, and wherein said dicistronic transcription/translation unit further comprises an internal ribosome binding site between the sequence encoding the protein and the sequence encoding the fusion protein,
(b) isolating said clones expressing said protein, and
(c) obtaining said expressed protein.

30. A method for producing a polypeptide having factor VIII activity comprising:
(a) transfecting SK-HEP-1 cells with an expression plasmid comprising the coding sequence of a polypeptide having factor VIII activity selected from the group consisting of full-length factor VIII, a factor VIII deletion mutant, factor VIII dB928, and a factor VIII derivative to obtain clones, wherein said expression plasmid comprises a dicistronic transcription/translation unit comprising:
(i) a sequence encoding said polypeptide having factor VIII activity, and
(ii) a sequence encoding a fusion protein comprising the coding sequence of a dominant selection marker gene and a dihydrofolate reductase (dhfr) gene that expresses a wild-type dhfr phenotype as an amplification marker, wherein said sequence encoding said fusion protein is located 3' to said sequence encoding said polypeptide having factor VIII activity and wherein said dicistronic transcription/translation unit further comprises an internal ribosome binding site between the sequence encoding said polypeptide having factor VIII activity and the sequence encoding the fusion protein,
(b) isolating said clones expressing said polypeptide having factor VIII activity, and
(c) obtaining said expressed polypeptide having factor VIII activity.

31. A method for producing a protein comprising:
(a) transfecting an eukaryotic cell line expressing an endogenous dihydrofolate reductase (dhfr) gene with an expression plasmid to obtain clones, wherein said expression plasmid comprises a dicistronic transcription/translation unit comprising:

(i) a sequence encoding said protein, wherein said protein is recombinant human prothrombin, recombinant human factor VIII, recombinant human FVIIIdB928, a recombinant human factor IX, recombinant human protein C, recombinant human von Willebrand factor or recombinant human serum albumin, and (ii) a sequence encoding a fusion protein comprising the coding sequence of a dominant selection marker gene and a dihydrofolate reductase (dhfr) gene that expresses a wild-type dhfr phenotype as an amplification marker, wherein said sequence encoding said fusion protein is located 3' to said sequence encoding said protein, and wherein said dicistronic transcription/translation unit further comprises an internal ribosome binding site between the sequence encoding the protein and the sequence encoding the fusion protein, (b) isolating said clones obtained by said transfection step controlled by said selection marker, (c) amplifying said selected clones in a first amplification, (d) subsequently further amplifying said clones in a further amplification controlled by said amplification marker, thereby expressing said protein, and (e) obtaining said expressed protein.

\* \* \* \* \*

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

CCACCCCCGC CTCCA                                                         15

(2) INFORMATION FOR SEQ ID NO: 2:

(i) SEQUENCE CHARACTERISTICS:
       (A) LENGTH: 15 base pairs
       (B) TYPE: nucleic acid
       (C) STRANDEDNESS: single
       (D) TOPOLOGY: linear (ii) MOLECULE TYPE: other nucleic acid
       (A) DESCRIPTION:   /desc = "synthetic"

(xi) SEQUENCE DESCRIPTION: SEQ ID NO: 2:

GGAGGCGGGG GTGGA                                                         15

(2) INFORMATION FOR SEQ ID NO: 3:

(i) SEQUENCE CHARACTERISTICS:
       (A) LENGTH: 524 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 3:

Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu

```
145                 150                 155                 160
Pro Glu Tyr Pro Gly Val Leu Ser Glu Val Gln Glu Lys Gly Ile
                165                 170                 175
Lys Tyr Lys Phe Glu Val Tyr Glu Lys Pro Glu Leu Thr Ala Thr
                180                 185                 190
Ser Val Glu Lys Phe Leu Ile Glu Lys Phe Asp Ser Val Ser Asp Leu
            195                 200                 205
Met Gln Leu Ser Glu Gly Glu Ser Arg Ala Phe Ser Phe Asp Val
        210                 215                 220
Gly Gly Arg Gly Tyr Val Leu Arg Val Asn Ser Cys Ala Asp Gly Phe
225                 230                 235                 240
Tyr Lys Asp Arg Tyr Val Tyr Arg His Phe Ala Ser Ala Ala Leu Pro
                245                 250                 255
Ile Pro Glu Val Leu Asp Ile Gly Glu Phe Ser Glu Ser Leu Thr Tyr
                260                 265                 270
Cys Ile Ser Arg Arg Ala Gln Gly Val Thr Leu Gln Asp Leu Pro Glu
        275                 280                 285
Thr Glu Leu Pro Ala Val Leu Gln Pro Val Ala Glu Ala Met Asp Ala
    290                 295                 300
Ile Ala Ala Asp Leu Ser Gln Thr Ser Gly Phe Gly Pro Phe Gly
305                 310                 315                 320
Pro Gln Gly Ile Gly Gln Tyr Thr Thr Trp Arg Asp Phe Ile Cys Ala
                325                 330                 335
Ile Ala Asp Pro His Val Tyr His Trp Gln Thr Val Met Asp Asp Thr
                340                 345                 350
Val Ser Ala Ser Val Ala Gln Ala Leu Asp Glu Leu Met Leu Trp Ala
    355                 360                 365
Glu Asp Cys Pro Glu Val Arg His Leu Val His Ala Asp Phe Gly Ser
    370                 375                 380
Asn Asn Val Leu Thr Asp Asn Gly Arg Ile Thr Ala Val Ile Asp Trp
385                 390                 395                 400
Ser Glu Ala Met Phe Gly Asp Ser Gln Tyr Glu Val Ala Asn Ile Phe
                405                 410                 415
Phe Trp Arg Pro Trp Leu Ala Cys Met Glu Gln Gln Thr Arg Tyr Phe
                420                 425                 430
Glu Arg Arg His Pro Glu Leu Ala Gly Ser Pro Arg Leu Arg Ala Tyr
            435                 440                 445
Met Leu Arg Ile Gly Leu Asp Gln Leu Tyr Gln Ser Leu Val Asp Gly
    450                 455                 460
Asn Phe Asp Asp Ala Ala Trp Ala Gln Gly Arg Cys Asp Ala Ile Val
465                 470                 475                 480
Arg Ser Gly Ala Gly Thr Val Gly Arg Thr Gln Ile Ala Arg Arg Ser
                485                 490                 495
Ala Ala Val Trp Thr Asp Gly Cys Val Glu Val Leu Ala Asp Ser Gly
            500                 505                 510
Asn Arg Arg Pro Ser Thr Arg Pro Arg Ala Lys Glu
        515                 520

(2) INFORMATION FOR SEQ ID NO: 4:

(i) SEQUENCE CHARACTERISTICS:
        (A) LENGTH: 539 amino acids
        (B) TYPE: amino acid
        (C) STRANDEDNESS: single
        (D) TOPOLOGY: linear
```

(ii) MOLECULE TYPE: protein (ix) FEATURE:
    (A) NAME/KEY: Peptide
    (B) LOCATION:192..196
    (D) OTHER INFORMATION:/note= ""Glycin Spacer""

(xi) SEQUENCE DESCRIPTION: SEQ ID NO: 4:

```
Met Val Arg Pro Leu Asn Cys Ile Val Ala Val Ser Gln Asn Met Gly
1               5                   10                  15

Ile Gly Lys Asn Gly Asp Leu Pro Trp Pro Leu Arg Asn Glu Phe
            20                  25                  30

Lys Tyr Phe Gln Arg Met Thr Thr Thr Ser Ser Val Glu Gly Lys Gln
            35                  40                  45

Asn Leu Val Ile Met Gly Arg Lys Thr Trp Phe Ser Ile Pro Glu Lys
50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
                100                 105                 110

Val Trp Ile Val Gly Gly Ser Ser Val Tyr Gln Glu Ala Met Asn Gln
                115                 120                 125

Pro Gly His Leu Arg Leu Phe Val Thr Arg Ile Met Gln Glu Phe Glu
                130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Gly Arg Leu Arg Thr Gly
                180                 185                 190

Gly Gly Gly Gly Asn Arg Arg Ile Pro Pro Glu Leu Thr Ala Thr Ser
                195                 200                 205

Val Glu Lys Phe Leu Ile Glu Lys Phe Asp Ser Val Ser Asp Leu Met
210                 215                 220

Gln Leu Ser Glu Gly Glu Ser Arg Ala Phe Ser Phe Asp Val Gly
225                 230                 235                 240

Gly Arg Gly Tyr Val Leu Arg Val Asn Ser Cys Ala Asp Gly Phe Tyr
                245                 250                 255

Lys Asp Arg Tyr Val Tyr Arg His Phe Ala Ser Ala Ala Leu Pro Ile
                260                 265                 270

Pro Glu Val Leu Asp Ile Gly Glu Phe Ser Glu Ser Leu Thr Tyr Cys
                275                 280                 285

Ile Ser Arg Arg Ala Gln Gly Val Thr Leu Gln Asp Leu Pro Glu Thr
                290                 295                 300

Glu Leu Pro Ala Val Leu Gln Pro Val Ala Glu Ala Met Asp Ala Ile
305                 310                 315                 320

Ala Ala Ala Asp Leu Ser Gln Thr Ser Gly Phe Gly Pro Phe Gly Pro
                325                 330                 335

Gln Gly Ile Gly Gln Tyr Thr Thr Trp Arg Asp Phe Ile Cys Ala Ile
                340                 345                 350

Ala Asp Pro His Val Tyr His Trp Gln Thr Val Met Asp Asp Thr Val
                355                 360                 365
```

```
Ser Ala Ser Val Ala Gln Ala Leu Asp Glu Leu Met Leu Trp Ala Glu
    370                 375                 380

Asp Cys Pro Glu Val Arg His Leu Val His Ala Asp Phe Gly Ser Asn
385                 390                 395                 400

Asn Val Leu Thr Asp Asn Gly Arg Ile Thr Ala Val Ile Asp Trp Ser
                405                 410                 415

Glu Ala Met Phe Gly Asp Ser Gln Tyr Glu Val Ala Asn Ile Phe Phe
            420                 425                 430

Trp Arg Pro Trp Leu Ala Cys Met Glu Gln Gln Thr Arg Tyr Phe Glu
        435                 440                 445

Arg Arg His Pro Glu Leu Ala Gly Ser Pro Arg Leu Arg Ala Tyr Met
    450                 455                 460

Leu Arg Ile Gly Leu Asp Gln Leu Tyr Gln Ser Leu Val Asp Gly Asn
465                 470                 475                 480

Phe Asp Asp Ala Ala Trp Ala Gln Gly Arg Cys Asp Ala Ile Val Arg
                485                 490                 495

Ser Gly Ala Gly Thr Val Gly Arg Thr Gln Ile Ala Arg Arg Ser Ala
            500                 505                 510

Ala Val Trp Thr Asp Gly Cys Val Glu Val Leu Ala Asp Ser Gly Asn
        515                 520                 525

Arg Arg Pro Ser Thr Arg Pro Arg Ala Lys Glu
    530                 535
```

(2) INFORMATION FOR SEQ ID NO: 5:

(i) SEQUENCE CHARACTERISTICS:
        (A) LENGTH: 539 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Peptide
        (B) LOCATION:190..194
        (D) OTHER INFORMATION:/note= ""Prolin Spacer""

(xi) SEQUENCE DESCRIPTION: SEQ ID NO: 5:

```
Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
    130                 135                 140

Ser Asp Thr Phe Phe Pro Glu Ile Asp Leu Gly Lys Tyr Lys Leu Leu
```

-continued

```
            145                 150                 155                 160
Pro Glu Tyr Pro Gly Val Leu Ser Glu Val Gln Glu Lys Gly Ile
                    165                 170                 175
Lys Tyr Lys Phe Glu Val Tyr Glu Lys Lys Gly Arg Phe Pro Pro
                180                 185                 190
Pro Pro Val Arg Asn Arg Ile Pro Pro Glu Leu Thr Ala Thr Ser
            195                 200                 205
Val Glu Lys Phe Leu Ile Glu Lys Phe Asp Ser Val Ser Asp Leu Met
        210                 215                 220
Gln Leu Ser Glu Gly Glu Ser Arg Ala Phe Ser Phe Asp Val Gly
225                 230                 235                 240
Gly Arg Gly Tyr Val Leu Arg Val Asn Ser Cys Ala Asp Gly Phe Tyr
                245                 250                 255
Lys Asp Arg Tyr Val Tyr Arg His Phe Ala Ser Ala Ala Leu Pro Ile
            260                 265                 270
Pro Glu Val Leu Asp Ile Gly Glu Phe Ser Glu Ser Leu Thr Tyr Cys
        275                 280                 285
Ile Ser Arg Arg Ala Gln Gly Val Thr Leu Gln Asp Leu Pro Glu Thr
    290                 295                 300
Glu Leu Pro Ala Val Leu Gln Pro Val Ala Glu Ala Met Asp Ala Ile
305                 310                 315                 320
Ala Ala Ala Asp Leu Ser Gln Thr Ser Gly Phe Gly Pro Phe Gly Pro
                325                 330                 335
Gln Gly Ile Gly Gln Tyr Thr Thr Trp Arg Asp Phe Ile Cys Ala Ile
                340                 345                 350
Ala Asp Pro His Val Tyr His Trp Gln Thr Val Met Asp Asp Thr Val
            355                 360                 365
Ser Ala Ser Val Ala Gln Ala Leu Asp Glu Leu Met Leu Trp Ala Glu
370                 375                 380
Asp Cys Pro Glu Val Arg His Leu Val His Ala Asp Phe Gly Ser Asn
385                 390                 395                 400
Asn Val Leu Thr Asp Asn Gly Arg Ile Thr Ala Val Ile Asp Trp Ser
                405                 410                 415
Glu Ala Met Phe Gly Asp Ser Gln Tyr Glu Val Ala Asn Ile Phe Phe
            420                 425                 430
Trp Arg Pro Trp Leu Ala Cys Met Glu Gln Gln Thr Arg Tyr Phe Glu
        435                 440                 445
Arg Arg His Pro Glu Leu Ala Gly Ser Pro Arg Leu Arg Ala Tyr Met
    450                 455                 460
Leu Arg Ile Gly Leu Asp Gln Leu Tyr Gln Ser Leu Val Asp Gly Asn
465                 470                 475                 480
Phe Asp Asp Ala Ala Trp Ala Gln Gly Arg Cys Asp Ala Ile Val Arg
                485                 490                 495
Ser Gly Ala Gly Thr Val Gly Arg Thr Gln Ile Ala Arg Arg Ser Ala
                500                 505                 510
Ala Val Trp Thr Asp Gly Cys Val Glu Val Leu Ala Asp Ser Gly Asn
            515                 520                 525
Arg Arg Pro Ser Thr Arg Pro Arg Ala Lys Glu
        530                 535
```

(2) INFORMATION FOR SEQ ID NO: 6:

(i) SEQUENCE CHARACTERISTICS:
        (A) LENGTH: 2079 base pairs (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 6:

```
ACCATATTGC CGTCTTTTGG CAATGTGAGG GCCCGGAAAC CTGGCCCTGT CTTCTTGACG      60

AGCATTCCTA GGGGTCTTTC CCCTCTCGCC AAAGGAATGC AAGGTCTGTT GAATGTCGTG     120

AAGGAAGCAG TTCCTCTGGA AGCTTCTTGA AGACAAACAA CGTCTGTAGC GACCCTTTGC     180

AGGCAGCGGA ACCCCCCACC TGGCGACAGG TGCCTCTGCG GCCAAAAGCC ACGTGTATAA     240

GATACACCTG CAAAGGCGGC ACAACCCCAG TGCCACGTTG TGAGTTGGAT AGTTGTGGAA     300

AGAGTCAAAT GGCTCTCCTC AAGCGTATTC AACAAGGGGC TGAAGGATGC CCAGAAGGTA     360

CCCCATTGTA TGGGATCTGA TCTGGGGCCT CGGTGCACAT GCTTTACATG TGTTTAGTCG     420

AGGTTAAAAA ACGTCTAGGC CCCCCGAACC ACGGGACGT GGTTTTCCTT TGAAAAACAC      480

GATAATACCA TGGTTCGACC ATTGAACTGC ATCGTCGCCG TGTCCCAAAA TATGGGGATT     540

GGCAAGAACG GAGACCTACC CTGGCCTCCG CTCAGGAACG AGTTCAAGTA CTTCCAAAGA     600

ATGACCACAA CCTCTTCAGT GGAAGGTAAA CAGAATCTGG TGATTATGGG TAGGAAAACC     660

TGGTTCTCCA TTCCTGAGAA GAATCGACCT TTAAAGGACA GAATTAATAT AGTTCTCAGT     720

AGAGAACTCA AAGAACCACC ACGAGGAGCT CATTTTCTTG CCAAAAGTTT GGATGATGCC     780

TTAAGACTTA TTGAACAACC GGAATTGGCA AGTAAAGTAG ACATGGTTTG GATAGTCGGA     840

GGCAGTTCTG TTTACCAGGA AGCCATGAAT CAACCAGGCC ATCTCAGACT CTTTGTGACA     900

AGGATCATGC AGGAATTTGA AAGTGACACG TTTTTCCCAG AAATTGATTT GGGGAAATAT     960

AAACTTCTCC CAGAATACCC AGGCGTCCTC TCTGAGGTCC AGGAGGAAAA AGGCATCAAG    1020

TATAAGTTTG AAGTCTACGA GAAGAAAGGT CGACGGATCC CGCCTGAACT CACCGCGACG    1080

TCTGTCGAGA AGTTTCTGAT CGAAAAGTTC GACAGCGTCT CCGACCTGAT GCAGCTCTCG    1140

GAGGGCGAAG AATCTCGTGC TTTCAGCTTC GATGTAGGAG GGCGTGGATA TGTCCTGCGG    1200

GTAAATAGCT GCGCCGATGG TTTTCTACAA AGATCGTTATG TTTATCGGCA CTTTGCATCG   1260

GCCGCGCTCC CGATTCCGGA AGTGCTTGAC ATTGGGGAAT TCAGCGAGAG CCTGACCTAT    1320

TGCATCTCCC GCCGTGCACA GGGTGTCACG TTGCAAGACC TGCCTGAAAC CGAACTGCCC    1380

GCTGTTCTGC AGCCGGTCGC GGAGGCCATG GATGCGATCG CTGCGGCCGA TCTTAGCCAG    1440

ACGAGCGGGT TCGGCCCATT CGGACCGCAA GGAATCGGTC AATACACTAC ATGGCGTGAT    1500

TTCATATGCG CGATTGCTGA TCCCCATGTG TATCACTGGC AAACTGTGAT GGACGACACC    1560

GTCAGTGCGT CCGTCGCGCA GGCTCTCGAT GAGCTGATGC TTTGGGCCGA GGACTGCCCC    1620

GAAGTCCGGC ACCTCGTGCA CGCGGATTTC GGCTCCAACA ATGTCCTGAC GGACAATGGC    1680

CGCATAACAG CGGTCATTGA CTGGAGCGAG GCGATGTTCG GGGATTCCCA ATACGAGGTC    1740

GCCAACATCT TCTTCTGGAG GCCGTGGTTG GCTTGTATGG AGCAGCAGAC GCGCTACTTC    1800

GAGCGGAGGC ATCCGGAGCT TGCAGGATCG CCGCGGCTCC GGGCGTATAT GCTCCGCATT    1860

GGTCTTGACC AACTCTATCA GAGCTTGGTT GACGGCAATT TCGATGATGC AGCTTGGGCG    1920

CAGGGTCGAT GCGACGCAAT CGTCCGATCC GGAGCCGGGA CTGTCGGGCG TACACAAATC    1980

GCCCGCAGAA GCGCGGCCGT CTGGACCGAT GGCTGTGTAG AAGTACTCGC CGATAGTGGA    2040

AACCGACGCC CCAGCACTCG TCCGAGGGCA AAGGAATAG                           2079
```

(2) INFORMATION FOR SEQ ID NO: 7:

(i) SEQUENCE CHARACTERISTICS:
        (A) LENGTH: 2109 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

```
ACCATATTGC CGTCTTTTGG CAATGTGAGG GCCCGGAAAC CTGGCCCTGT CTTCTTGACG         60

AGCATTCCTA GGGGTCTTTC CCCTCTCGCC AAAGGAATGC AAGGTCTGTT GAATGTCGTG        120

AAGGAAGCAG TTCCTCTGGA AGCTTCTTGA AGACAAACAA CGTCTGTAGC GACCCTTTGC        180

AGGCAGCGGA ACCCCCCACC TGGCGACAGG TGCCTCTGCG GCCAAAAGCC ACGTGTATAA        240

GATACACCTG CAAAGGCGGC ACAACCCCAG TGCCACGTTG TGAGTTGGAT AGTTGTGGAA        300

AGAGTCAAAT GGCTCTCCTC AAGCGTATTC AACAAGGGGC TGAAGGATGC CCAGAAGGTA        360

CCCCATTGTA TGGGATCTGA TCTGGGGCCT CGGTGCACAT GCTTTACATG TGTTTAGTCG        420

AGGTTAAAAA ACGTCTAGGC CCCCCGAACC ACGGGGACGT GGTTTTCCTT TGAAAAACAC        480

GATAATACCA TGGTTCGACC ATTGAACTGC ATCGTCGCCG TGTCCCAAAA TATGGGGATT        540

GGCAAGAACG GAGACCTACC CTGGCCTCCG CTCAGGAACG AGTTCAAGTA CTTCCAAAGA        600

ATGACCACAA CCTCTTCAGT GGAAGGTAAA CAGAATCTGG TGATTATGGG TAGGAAAACC        660

TGGTTCTCCA TTCCTGAGAA GAATCGACCT TTAAAGGACA GAATTAATAT AGTTCTCAGT        720

AGAGAACTCA AAGAACCACC ACGAGGAGCT CATTTTCTTG CCAAAAGTTT GGATGATGCC        780

TTAAGACTTA TTGAACAACC GGAATTGGCA AGTAAAGTAG ACATGGTTTG GATAGTCGGA        840

GGCAGTTCTG TTTACCAGGA AGCCATGAAT CAACCAGGCC ATCTCAGACT CTTTGTGACA        900

AGGATCATGC AGGAATTTGA AAGTGACACG TTTTTCCCAG AAATTGATTT GGGGAAATAT        960

AAACTTCTCC CAGAATACCC AGGCGTCCTC TCTGAGGTCC AGGAGGAAAA AGGCATCAAG       1020

TATAAGTTTG AAGTCTACGA GAAGAAAGGT CGATTACGTA CTGGAGGCGG GGGTGGAAAT       1080

CGACGGATCC CGCCTGAACT CACCGCGACG TCTGTCGAGA AGTTTCTGAT CGAAAAGTTC       1140

GACAGCGTCT CCGACCTGAT GCAGCTCTCG GAGGGCGAAG AATCTCGTGC TTTCAGCTTC       1200

GATGTAGGAG GCGTGGATA TGTCCTGCGG GTAAATAGCT GCGCCGATGG TTTCTACAAA        1260

GATCGTTATG TTTATCGGCA CTTTGCATCG GCCGCGCTCC CGATTCCGGA AGTGCTTGAC       1320

ATTGGGGAAT TCAGCGAGAG CCTGACCTAT TGCATCTCCC GCCGTGCACA GGGTGTCACG       1380

TTGCAAGACC TGCCTGAAAC CGAACTGCCC GCTGTTCTGC AGCCGGTCGC GGAGGCCATG       1440

GATGCGATCG CTGCGGCCGA TCTTAGCCAG ACGAGCGGGT TCGGCCCATT CGGACCGCAA       1500

GGAATCGGTC AATACACTAC ATGGCGTGAT TTCATATGCG CGATTGCTGA TCCCCATGTG       1560

TATCACTGGC AAACTGTGAT GGACGACACC GTCAGTGCGT CCGTCGCGCA GGCTCTCGAT       1620

GAGCTGATGC TTTGGGCCGA GGACTGCCCC GAAGTCCGGC ACCTCGTGCA CGCGGATTTC       1680

GGCTCCAACA ATGTCCTGAC GGACAATGGC CGCATAACAG CGGTCATTGA CTGGAGCGAG       1740

GCGATGTTCG GGGATTCCCA ATACGAGGTC GCCAACATCT TCTTCTGGAG GCCGTGGTTG       1800

GCTTGTATGG AGCAGCAGAC GCGCTACTTC GAGCGGAGGC ATCCGGAGCT TGCAGGATCG       1860

CCGCGGCTCC GGGCGTATAT GCTCCGCATT GGTCTTGACC AACTCTATCA GAGCTTGGTT       1920

GACGGCAATT TCGATGATGC AGCTTGGGCG CAGGGTCGAT GCGACGCAAT CGTCCGATCC       1980

GGAGCCGGGA CTGTCGGGCG TACACAAATC GCCCGCAGAA GCGCGGCCGT CTGGACCGAT       2040
```

```
GGCTGTGTAG AAGTACTCGC CGATAGTGGA AACCGACGCC CCAGCACTCG TCCGAGGGCA    2100

AAGGAATAG                                                          2109

(2) INFORMATION FOR SEQ ID NO: 8:

(i) SEQUENCE CHARACTERISTICS:
        (A) LENGTH: 2109 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

ACCATATTGC CGTCTTTTGG CAATGTGAGG GCCCGGAAAC CTGGCCCTGT CTTCTTGACG     60

AGCATTCCTA GGGGTCTTTC CCCTCTCGCC AAAGGAATGC AAGGTCTGTT GAATGTCGTG    120

AAGGAAGCAG TTCCTCTGGA AGCTTCTTGA AGACAAACAA CGTCTGTAGC GACCCTTTGC    180

AGGCAGCGGA ACCCCCACCT TGGCGACAGG TGCCTCTGCG GCCAAAAGCC ACGTGTATAA    240

GATACACCTG CAAAGGCGGC ACAACCCCAG TGCCACGTTG TGAGTTGGAT AGTTGTGGAA    300

AGAGTCAAAT GGCTCTCCTC AAGCGTATTC AACAAGGGGC TGAAGGATGC CCAGAAGGTA    360

CCCCATTGTA TGGGATCTGA TCTGGGGCCT CGGTGCACAT GCTTTACATG TGTTTAGTCG    420

AGGTTAAAAA ACGTCTAGGC CCCCCGAACC ACGGGGACGT GGTTTTCCTT TGAAAAACAC    480

GATAATACCA TGGTTCGACC ATTGAACTGC ATCGTCGCCG TGTCCCAAAA TATGGGGATT    540

GGCAAGAACG GAGACCTACC CTGGCCTCCG CTCAGGAACG AGTTCAAGTA CTTCCAAAGA    600

ATGACCACAA CCTCTTCAGT GGAAGGTAAA CAGAATCTGG TGATTATGGG TAGGAAAACC    660

TGGTTCTCCA TTCCTGAGAA GAATCGACCT TTAAAGGACA GAATTAATAT AGTTCTCAGT    720

AGAGAACTCA AGAACCACC ACGAGGAGCT CATTTTCTTG CCAAAAGTTT GGATGATGCC    780

TTAAGACTTA TTGAACAACC GGAATTGGCA AGTAAAGTAG ACATGGTTTG GATAGTCGGA    840

GGCAGTTCTG TTTACCAGGA AGCCATGAAT CAACCAGGCC ATCTCAGACT CTTTGTGACA    900

AGGATCATGC AGGAATTTGA AAGTGACACG TTTTTCCCAG AAAATTGATTT GGGGAAATAT    960

AAACTTCTCC CAGAATACCC AGGCGTCCTC TCTGAGGTCC AGGAGGAAAA AGGCATCAAG   1020

TATAAGTTTG AAGTCTACGA GAAGAAAGGT CGATTTCCAC CCCCGCCTCC AGTACGTAAT   1080

CGACGGATCC CGCCTGAACT CACCGCGACG TCTGTCGAGA AGTTTCTGAT CGAAAAGTTC   1140

GACAGCGTCT CCGACCTGAT GCAGCTCTCG GAGGGCGAAG AATCTCGTGC TTTCAGCTTC   1200

GATGTAGGAG GGCGTGGATA TGTCCTGCGG GTAAATAGCT GCGCCGATGG TTTCTACAAA   1260

GATCGTTATG TTTATCGGCA CTTTGCATCG GCCGCGCTCC CGATTCCGGA AGTGCTTGAC   1320

ATTGGGGAAT TCAGCGAGAG CCTGACCTAT GCATCTCCC GCCGTGCACA GGGTGTCACG   1380

TTGCAAGACC TGCCTGAAAC CGAACTGCCC GCTGTTCTGC AGCCGGTCGC GGAGGCCATG   1440

GATGCGATCG CTGCGGCCGA TCTTAGCCAG ACGAGCGGGT TCGGCCCATT CGGACCGCAA   1500

GGAATCGGTC AATACACTAC ATGGCGTGAT TTCATATGCG CGATTGCTGA TCCCCATGTG   1560

TATCACTGGC AAACTGTGAT GGACGACACC GTCAGTGCGT CCGTCGCGCA GGCTCTCGAT   1620

GAGCTGATGC TTTGGGCCGA GGACTGCCCC GAAGTCCGGC ACCTCGTGCA CGCGGATTTC   1680

GGCTCCAACA ATGTCCTGAC GGACAATGGC CGCATAACAG CGGTCATTGA CTGGAGCGAG   1740

GCGATGTTCG GGGATTCCCA ATACGAGGTC GCCAACATCT TCTTCTGGAG GCCGTGGTTG   1800

GCTTGTATGG AGCAGCAGAC GCGCTACTTC GAGCGGAGGC ATCCGGAGCT TGCAGGATCG   1860
```

```
CCGCGGCTCC GGGCGTATAT GCTCCGCATT GGTCTTGACC AACTCTATCA GAGCTTGGTT        1920

GACGGCAATT TCGATGATGC AGCTTGGGCG CAGGGTCGAT GCGACGCAAT CGTCCGATCC        1980

GGAGCCGGGA CTGTCGGGCG TACACAAATC GCCCGCAGAA GCGCGGCCGT CTGGACCGAT        2040

GGCTGTGTAG AAGTACTCGC CGATAGTGGA AACCGACGCC CCAGCACTCG TCCGAGGGCA        2100

AAGGAATAG                                                                2109
```

(2) INFORMATION FOR SEQ ID NO: 9:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
TCGACCATGG ACAAGCTTAT CGATCCCGGG AATTCGGTAC CGTCGACCTG CAGGTGCACG         60

GGCCCAGATC TGACTGACTG A                                                   81
```

(2) INFORMATION FOR SEQ ID NO: 10:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
TCGATCAGTC AGTCAGATCT GGGCCCGTGC ACCTGCAGGT CGACGGTACC GAATTCCCGG         60

GATCGATAAG CTTGTCCATG G                                                   81
```

(2) INFORMATION FOR SEQ ID NO: 11:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
GGCCTAGGGC CCTAGGCCTA CTAGTACTAA GCTTCTGCAG GTCGACTCTA GAGGACCCCG         60

GGGAATTCAA TCGATGGCC                                                      79
```

(2) INFORMATION FOR SEQ ID NO: 12:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
ACCCCCGGGG GTACCATATT GCCGTCTTTT GG                                       32
```

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GGAATTCCCA TGGTATTATC GTGTTTTTC                                    29

(2) INFORMATION FOR SEQ ID NO: 14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GGAAGCTTGG CCATGGTTCG ACCATTGAAC TGC                               33

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GGTCAAGCTT TTCTTCTCGT AGACTTCAAA CTTATACT                          38

(2) INFORMATION FOR SEQ ID NO: 16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

TCGATTACGT ACTGGAGGCG GGGGTGGAAA                                   30

(2) INFORMATION FOR SEQ ID NO: 17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

TCGATTTCCA CCCCCGCCTC CAGTACGTAA                                   30

(2) INFORMATION FOR SEQ ID NO: 18:

(i) SEQUENCE CHARACTERISTICS:
        (A) LENGTH: 43 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO: 18:

GTCGATTACG TACTGGAGGC GGGGGTGGAA ATCGACGGAT CCC                43

(2) INFORMATION FOR SEQ ID NO: 19:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GTCGATTTCC ACCCCCGCCT CCAGTACGTA ATCGACGGAT CCC                43

(2) INFORMATION FOR SEQ ID NO: 20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GGAAATATGG CTTCTACACA CATGTGTTCC GCCTGAA                       37

(2) INFORMATION FOR SEQ ID NO: 21:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

TCCGTTCTTG CCAATCCCCA TATTTTGGGA CACGGCG                       37

(2) INFORMATION FOR SEQ ID NO: 22:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

TCGATGTTAA CTACGTAGCT AGCGCGGCCG CCGTACGTCG CGAGTCGACA ATATTGATAT    60

CGGTACCGGT ACCACTAGTG T                                             81

(2) INFORMATION FOR SEQ ID NO: 23:

(i) SEQUENCE CHARACTERISTICS:
        (A) LENGTH: 79 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO: 23:

CGACACTAGT GGTACCGGTA CCGATATCAA TATTGTCGAC TCGCGACGTA CGGCGGCCGC    60

GCTAGCTACG TAGTTAACA                                                79

(2) INFORMATION FOR SEQ ID NO: 24:

(i) SEQUENCE CHARACTERISTICS:
            (A) LENGTH: 79 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 24:

TCGAATCGAT TGAATTCCCC GGGGTCCTCT AGAGTCGACC TGCAGAAGCT TAGTACTAGT    60

AGGCCTAGGG CCCTATCGA                                                79

(2) INFORMATION FOR SEQ ID NO: 25:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 25:

TGTGAGCTGC CCCATGGTGG AGGCACTGGC                                    30

(2) INFORMATION FOR SEQ ID NO: 26:

(i) SEQUENCE CHARACTERISTICS:
            (A) LENGTH: 57 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 26:

GTGGAAGGAG GCGACCATGG GCCCCCCACT GTCGCCCTCG CAGGCATCCT GCCGGTC       57

(2) INFORMATION FOR SEQ ID NO: 27:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 27:

GCAGTCGCAG CTGAAGCTGC CGAT                                          24

(2) INFORMATION FOR SEQ ID NO: 28:

(i) SEQUENCE CHARACTERISTICS:
            (A) LENGTH: 80 base pairs
            (B) TYPE: nucleic acid
            (C) STRANDEDNESS: single
            (D) TOPOLOGY: linear -continued (ii) MOLECULE TYPE: DNA (genomic)

(xi) SEQUENCE DESCRIPTION: SEQ ID NO: 28:

TCGACCATGG AAGCTTATCG ATCCCGGGAA TTCGGTACCG TCGACCTTGC AGGTGCACGG    60

GCCCAGATCT GACTGATCGA    80

(2) INFORMATION FOR SEQ ID NO: 29:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 29:

GGCGACAGTC GGGGG    15

(2) INFORMATION FOR SEQ ID NO: 30:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 30:

Gly Asp Ser Gly Gly
1           5